US010266600B2

(12) United States Patent
Fricke et al.

(10) Patent No.: US 10,266,600 B2
(45) Date of Patent: Apr. 23, 2019

(54) DIAGNOSTIC ANTI-CD95L ANTIBODY

(71) Applicant: APOGENIX AG, Heidelberg (DE)

(72) Inventors: Harald Fricke, Mannheim (DE); Christian Gieffers, Dossenheim (DE); Jaromir Sykora, Heidelberg (DE)

(73) Assignee: APOGENIX AG, Heidelberg (DE)

( * ) Notice: Subject to any disclaimer, the term of this patent is extended or adjusted under 35 U.S.C. 154(b) by 0 days.

(21) Appl. No.: 15/335,297

(22) Filed: Oct. 26, 2016

(65) Prior Publication Data

US 2017/0044264 A1    Feb. 16, 2017

Related U.S. Application Data

(63) Continuation of application No. PCT/EP2015/059354, filed on Apr. 29, 2015.

(30) Foreign Application Priority Data

Apr. 29, 2014   (WO) ................ PCT/EP2014/058746

(51) Int. Cl.
    *G01N 33/574* (2006.01)
    *C07K 16/28* (2006.01)
    *A61K 39/00* (2006.01)

(52) U.S. Cl.
    CPC ... *C07K 16/2875* (2013.01); *G01N 33/57484* (2013.01); *G01N 33/57492* (2013.01); *A61K 2039/505* (2013.01); *C07K 2317/32* (2013.01); *C07K 2317/565* (2013.01); *G01N 2333/70575* (2013.01); *G01N 2800/52* (2013.01); *G01N 2800/54* (2013.01)

(58) Field of Classification Search
    CPC .......................... C07K 16/2875; G01N 33/574
    USPC ..................................................... 424/139.1
    See application file for complete search history.

(56) References Cited

U.S. PATENT DOCUMENTS

| 2003/0078228 A1 | 4/2003 | Taylor et al. |
| 2005/0048467 A1 | 3/2005 | Sastry et al. |
| 2010/0322922 A1 | 12/2010 | Martin-Villalba et al. |
| 2016/0103132 A1 | 4/2016 | Fricke et al. |

FOREIGN PATENT DOCUMENTS

| WO | 01/41803 A1 | 6/2001 |
| WO | 03/079750 A2 | 10/2003 |
| WO | 2008/080623 A2 | 7/2008 |
| WO | 2010/066914 A2 | 6/2010 |
| WO | 2012/125807 A2 | 9/2012 |
| WO | 2013/022995 A2 | 2/2013 |
| WO | 2014013037 A1 | 1/2014 |
| WO | 2014013039 A1 | 1/2014 |

OTHER PUBLICATIONS

Harmsen and Haard (Appl Microbiol Biotechnol 2007, 77:13-22).*
Aoki et al., "Restricted expression of an adenoviral vector encoding Fas ligand (CD95L) enhances safety for cancer gene therapy", Molecular Therapy, vol. 1, No. 6, Jun. 2000, pp. 555-565.
Jang, "Expression of CD40 and Fas Ligand in Bowen's Disease, Squamous Cell Carcinoma and Basal Cell Carcinoma", Yonsei Medical Journal, vol. 43, No. 3, pp. 304-308 (2002).
Reimer et al., "Fast:Fas Ratio—A Prognostic Factor in Breast Carcinomas", Cancer Research 60, pp. 822-828 (2000).
Shiraki et al., "Expression of Fas ligand in liver metastases of human colonic adenocarcinomas.", Proc Natl Acad Sci U S A. vol. 94, Jun. 1997, pp. 6420-6425.
Sigel et al., "Immunohistochemical Analysis of CD30-Positive Lymphoproliferative Disorders for Expression of CD95 and CD95L", Modem Pathology 13(4), pp. 446-451 (2000).
Hartmann et al., "Regular Article Transplantation Recombinant CD95-Fc (APG101) prevents graft-versus-host disease in mice without disabling antitumor cytotoxicity and T-cell functions", Blood, vol. 121, Jan. 1, 2013, pp. 556-565.
Wu et al., "Altered expression of survivin, fas and fasl contributed to cervicl cancer development and metastasis", Uropean Review for Medical and Pharmacological Sciences, vol. 16, Jan. 1, 2012, pp. 2004-2025.
International Search Report dated Jul. 14, 2015 in International Application No. PCT/EP2015/059354.

* cited by examiner

*Primary Examiner* — Yan Xiao
(74) *Attorney, Agent, or Firm* — Perkins Coie LLP; Viola T. Kung

(57) ABSTRACT

The present invention relates to a specific CD95L antibody and to the use thereof in the diagnosis of a cancer disease.

12 Claims, 11 Drawing Sheets

(4 of 11 Drawing Sheet(s) Filed in Color)

Specification includes a Sequence Listing.

Figure 4
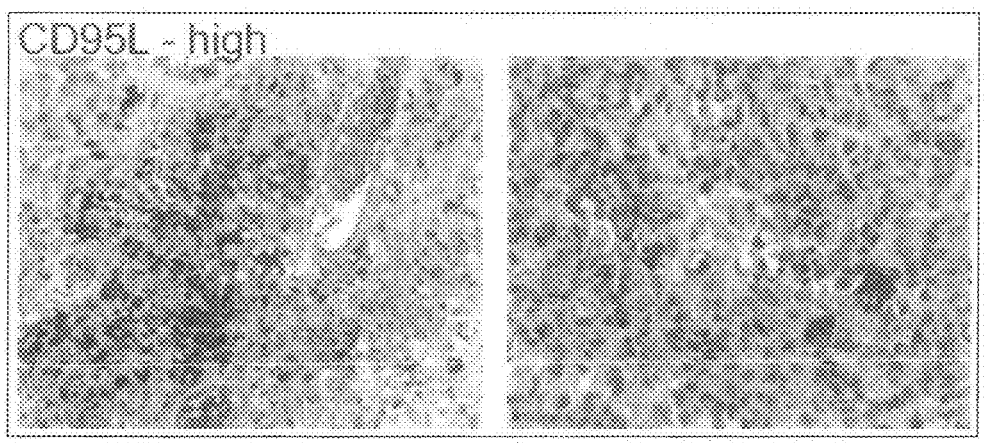
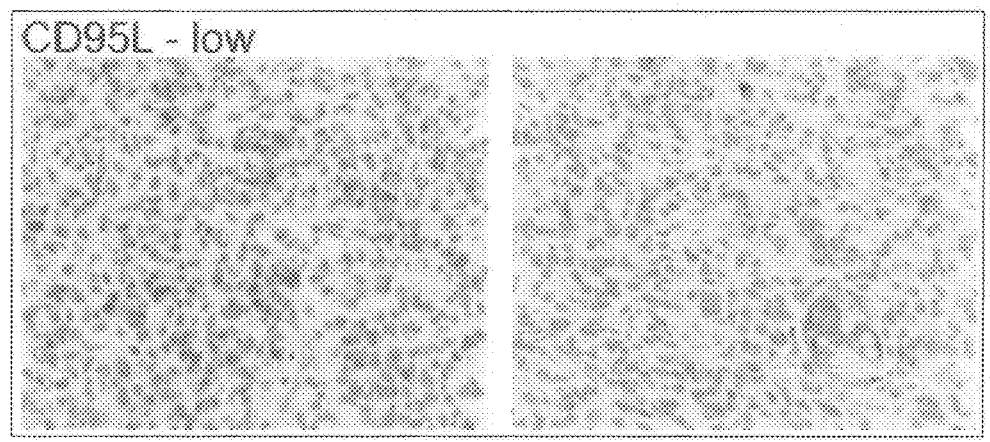

Figure 5: Comparison of purified anti CD95L monoclonal rabbit antibodies.
A
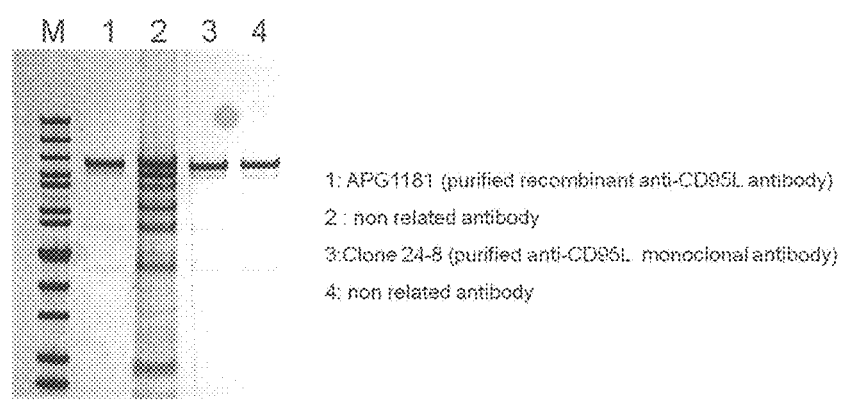
1: APG1181 (purified recombinant anti-CD95L antibody)
2: non related antibody
3: Clone 24-8 (purified anti-CD95L monoclonal antibody)
4: non related antibody
B
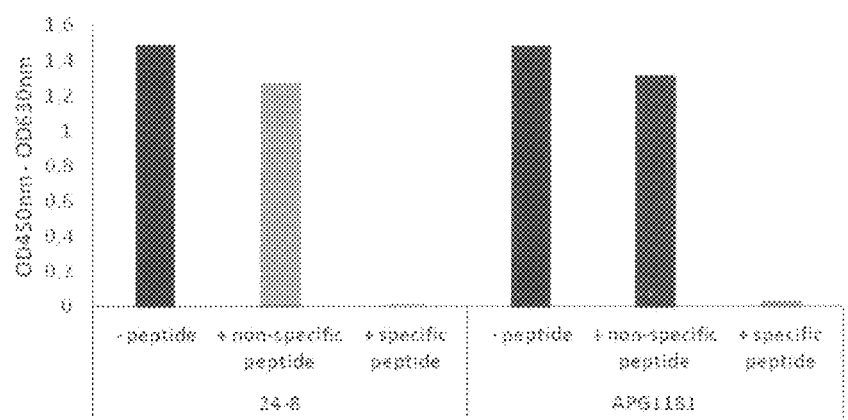

Figure 6: Specificity of anti-CD95L rabbit monoclonal antibody in IHC-based analysis
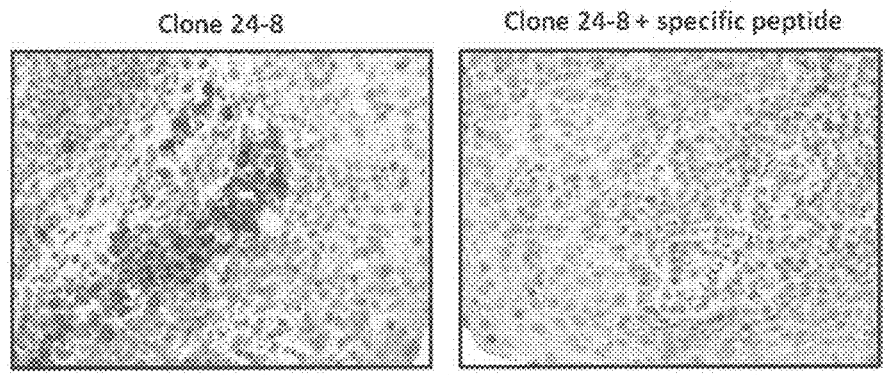

Figure 7: Comparison of purified antibodies anti CD95L monoclonal rabbit antibodies
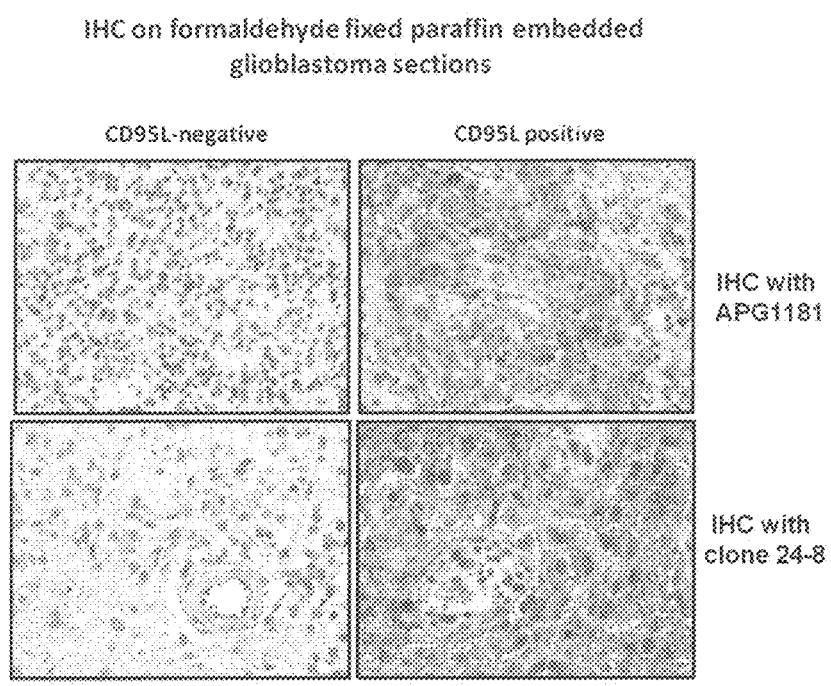

Figure 8: Peptides used for epitope mapping of the CD95L-antibody

```
              5         10        15        20
1)     MQQPFNYPYPQIYWVDSSASS-C        CD95L_NT (1-21)
2)     MQQPFNYPYP-C                   CD95L_NT (1-10)
3)         FNYPYPQIYW-C               CD95L_NT (5-14)
4)               QIYWVDSSASS-C        CD95L_NT (11-21)
5)                 YWVDSS-C           CD95L_NT (13-18)
6)                 YWVDSSA-C          CD95L_NT (13-19)
7)                  WVDSSA-C          CD95L_NT (14-19)
8)                IYWVDSSASS-C        CD95L_NT (12-21)
9)                ISWVDSSASS-C        CD95L_NT (12-21 Y-S)
10)               IYFVDSSASS-C        CD95L_NT (12-21 W-F)
11)               IYFVDSSVSS-C        CD95L_NT (12-21 A-V)
```

Figure 9: Epitope mapping of anti-CD95L rabbit monoclonal antibody (APG1181).
A
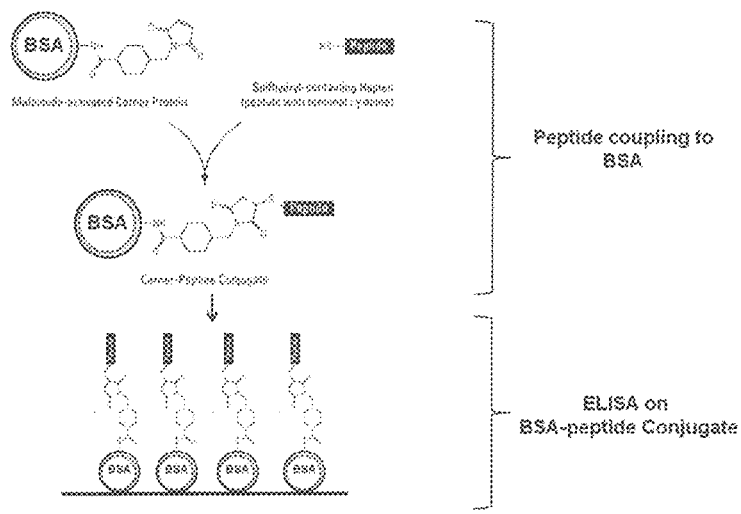
B
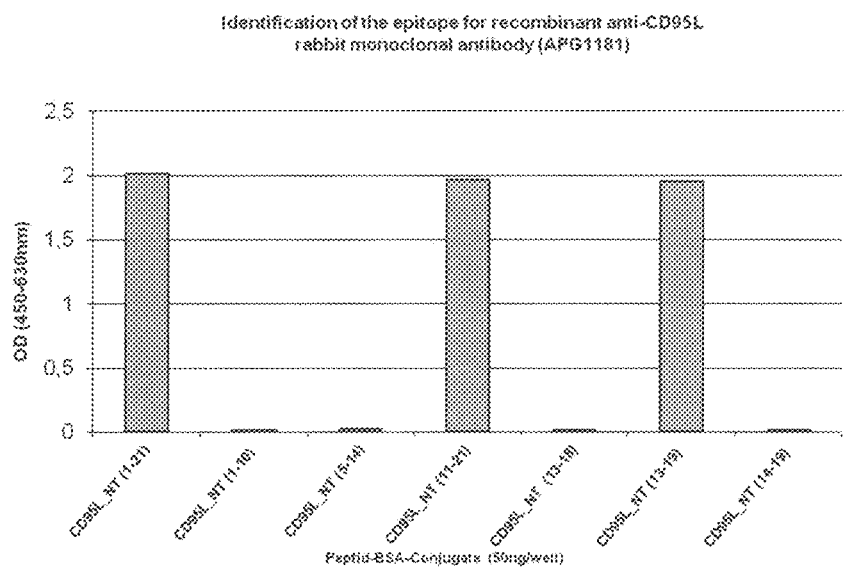

Figure 10: Fine mapping of the epitope for anti-CD95L rabbit monoclonal antibody (APG1181).
A
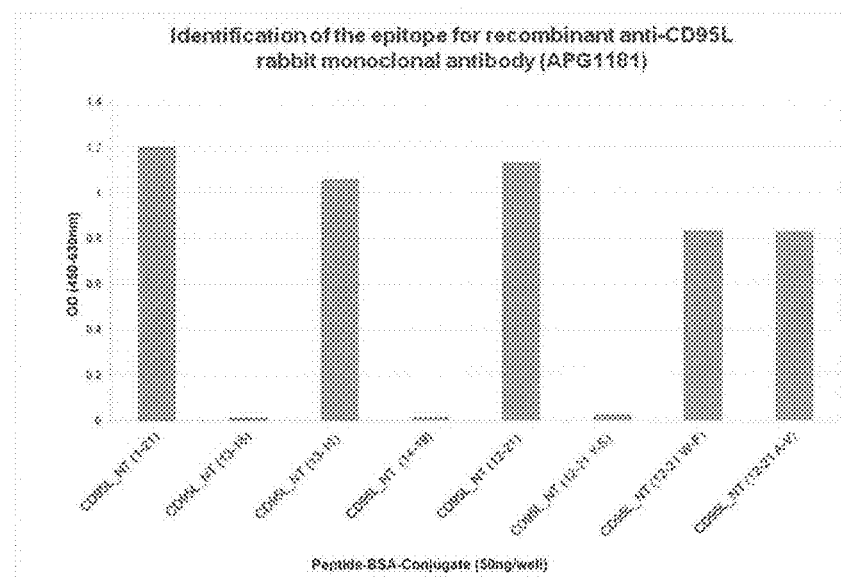
B
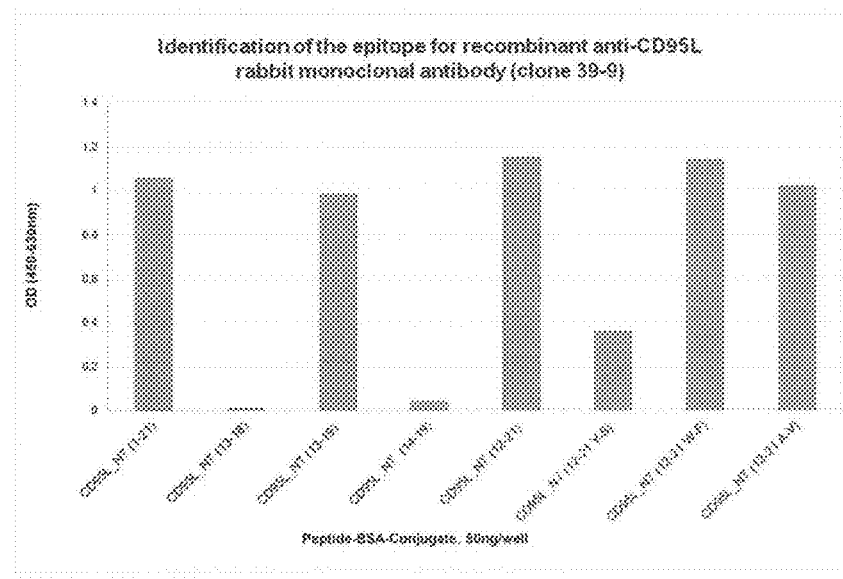

Figure 11: Comparison of the specificity of anti-CD95L rabbit monoclonal antibodies in IHC-based analysis.
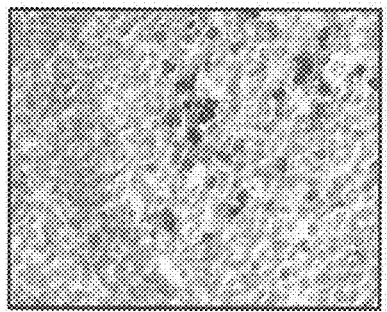
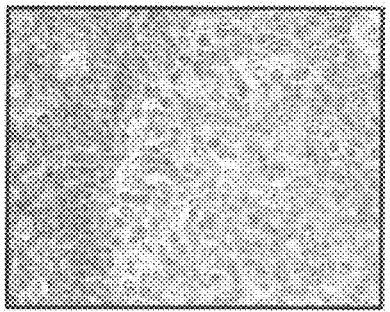

SEQUENCE LISTING

```
<160> NUMBER OF SEQ ID NOS: 25

<210> SEQ ID NO 1
<211> LENGTH: 6
<212> TYPE: PRT
<213> ORGANISM: artificial sequence
<220> FEATURE:
<223> OTHER INFORMATION: CDR-H1

<400> SEQUENCE: 1

Ser Ser Ala Trp Ile Cys
1               5

<210> SEQ ID NO 2
<211> LENGTH: 18
<212> TYPE: PRT
<213> ORGANISM: artificial sequence
<220> FEATURE:
<223> OTHER INFORMATION: CDR-H2

<400> SEQUENCE: 2

Cys Ile Phe Thr Gly Asn Ser Asp Ile Thr Ile Tyr Ala Asn Trp Ala
1               5                   10                  15

Lys Gly

<210> SEQ ID NO 3
<211> LENGTH: 7
```

```
<212> TYPE: PRT
<213> ORGANISM: artificial sequence
<220> FEATURE:
<223> OTHER INFORMATION: CDR-H3

<400> SEQUENCE: 3

Asn Leu Ala Ala Thr Lys Leu
1               5

<210> SEQ ID NO 4
<211> LENGTH: 11
<212> TYPE: PRT
<213> ORGANISM: artificial sequence
<220> FEATURE:
<223> OTHER INFORMATION: CDR-L1

<400> SEQUENCE: 4

Gln Ala Ser Gln Ser Ile Thr Asp Gln Leu Ser
1               5                   10

<210> SEQ ID NO 5
<211> LENGTH: 7
<212> TYPE: PRT
<213> ORGANISM: artificial sequence
<220> FEATURE:
<223> OTHER INFORMATION: CDR-L2

<400> SEQUENCE: 5

Arg Ala Ser Thr Leu Ala Ser
1               5

<210> SEQ ID NO 6
<211> LENGTH: 13
<212> TYPE: PRT
<213> ORGANISM: artificial sequence
<220> FEATURE:
<223> OTHER INFORMATION: CDR-L3

<400> SEQUENCE: 6

Leu Gly Val His Gly Tyr Ser Ser Asp Asp Ala Ile Ser
1               5                   10

<210> SEQ ID NO 7
<211> LENGTH: 117
<212> TYPE: PRT
<213> ORGANISM: artificial sequence
<220> FEATURE:
<223> OTHER INFORMATION: vH
<220> FEATURE:
<221> NAME/KEY: MISC_FEATURE
<222> LOCATION: (1)..(30)
<223> OTHER INFORMATION: HFR1
<220> FEATURE:
<221> NAME/KEY: MISC_FEATURE
<222> LOCATION: (31)..(36)
<223> OTHER INFORMATION: CDR-H1
<220> FEATURE:
<221> NAME/KEY: MISC_FEATURE
<222> LOCATION: (37)..(50)
<223> OTHER INFORMATION: HFR-2
<220> FEATURE:
<221> NAME/KEY: MISC_FEATURE
<222> LOCATION: (51)..(68)
<223> OTHER INFORMATION: CDR-H2
<220> FEATURE:
<221> NAME/KEY: MISC_FEATURE
<222> LOCATION: (69)..(99)
<223> OTHER INFORMATION: HFR3
<220> FEATURE:
<221> NAME/KEY: MISC_FEATURE
<222> LOCATION: (100)..(106)
```

```
<223> OTHER INFORMATION: CDR-H3
<220> FEATURE:
<221> NAME/KEY: MISC_FEATURE
<222> LOCATION: (107)..(117)
<223> OTHER INFORMATION: HFR-4

<400> SEQUENCE: 7

Gln Glu Gln Leu Glu Glu Ser Gly Gly Asp Leu Val Lys Pro Gly Ala
1               5                   10                  15

Ser Leu Thr Leu Thr Cys Thr Ala Ser Gly Phe Ser Phe Ser Ser Ser
            20                  25                  30

Ala Trp Ile Cys Trp Val Arg Gln Ala Pro Gly Lys Gly Leu Glu Trp
        35                  40                  45

Ile Ala Cys Ile Phe Thr Gly Asn Ser Asp Ile Thr Ile Tyr Ala Asn
    50                  55                  60

Trp Ala Lys Gly Arg Ser Thr Ile Ser Arg Thr Ser Thr Thr Val
65                  70                  75                  80

Thr Leu Gln Val Thr Ser Leu Thr Ala Ala Asp Thr Ala Thr Tyr Phe
                85                  90                  95

Cys Ala Arg Asn Leu Ala Ala Thr Lys Leu Trp Gly Pro Gly Thr Leu
            100                 105                 110

Val Thr Val Ser Ser
        115

<210> SEQ ID NO 8
<211> LENGTH: 111
<212> TYPE: PRT
<213> ORGANISM: artificial sequence
<220> FEATURE:
<223> OTHER INFORMATION: vL
<220> FEATURE:
<221> NAME/KEY: MISC_FEATURE
<222> LOCATION: (1)..(22)
<223> OTHER INFORMATION: LFR1
<220> FEATURE:
<221> NAME/KEY: MISC_FEATURE
<222> LOCATION: (23)..(33)
<223> OTHER INFORMATION: CDR-L1
<220> FEATURE:
<221> NAME/KEY: MISC_FEATURE
<222> LOCATION: (34)..(48)
<223> OTHER INFORMATION: LFR-2
<220> FEATURE:
<221> NAME/KEY: MISC_FEATURE
<222> LOCATION: (49)..(55)
<223> OTHER INFORMATION: CDR-L2
<220> FEATURE:
<221> NAME/KEY: MISC_FEATURE
<222> LOCATION: (56)..(87)
<223> OTHER INFORMATION: LFR3
<220> FEATURE:
<221> NAME/KEY: MISC_FEATURE
<222> LOCATION: (88)..(100)
<223> OTHER INFORMATION: CDR-L3
<220> FEATURE:
<221> NAME/KEY: MISC_FEATURE
<222> LOCATION: (101)..(111)
<223> OTHER INFORMATION: LFR4

<400> SEQUENCE: 8

Leu Val Met Thr Gln Thr Pro Ala Ser Val Ser Ala Ala Val Gly Gly
1               5                   10                  15

Thr Val Thr Ile Ser Cys Gln Ala Ser Gln Ser Ile Thr Asp Gln Leu
            20                  25                  30

Ser Trp Tyr Gln His Gln Pro Gly Gln Pro Pro Lys Leu Leu Ile Tyr
        35                  40                  45
```

```
Arg Ala Ser Thr Leu Ala Ser Gly Val Pro Ser Arg Phe Ser Gly Ser
 50                  55                  60
Gly Ser Glu Thr Glu Phe Ser Leu Thr Ile Ser Gly Leu Gln Cys Ala
 65                  70                  75                  80
Asp Ala Ala Thr Tyr Tyr Cys Leu Gly Val His Gly Tyr Ser Ser Asp
                     85                  90                  95
Asp Ala Ile Ser Phe Gly Gly Gly Thr Glu Val Val Val Lys Gly
                100                 105                 110
```

<210> SEQ ID NO 9
<211> LENGTH: 440
<212> TYPE: PRT
<213> ORGANISM: artificial sequence
<220> FEATURE:
<223> OTHER INFORMATION: mature peptide: heavy chain
<220> FEATURE:
<221> NAME/KEY: DOMAIN
<222> LOCATION: (1)..(117)
<223> OTHER INFORMATION: vH

<400> SEQUENCE: 9

```
Gln Glu Gln Leu Glu Glu Ser Gly Gly Asp Leu Val Lys Pro Gly Ala
 1                   5                  10                  15
Ser Leu Thr Leu Thr Cys Thr Ala Ser Gly Phe Ser Phe Ser Ser Ser
                 20                  25                  30
Ala Trp Ile Cys Trp Val Arg Gln Ala Pro Gly Lys Gly Leu Glu Trp
             35                  40                  45
Ile Ala Cys Ile Phe Thr Gly Asn Ser Asp Ile Thr Ile Tyr Ala Asn
         50                  55                  60
Trp Ala Lys Gly Arg Ser Thr Ile Ser Arg Thr Ser Ser Thr Thr Val
 65                  70                  75                  80
Thr Leu Gln Val Thr Ser Leu Thr Ala Ala Asp Thr Ala Thr Tyr Phe
                 85                  90                  95
Cys Ala Arg Asn Leu Ala Ala Thr Lys Leu Trp Gly Pro Gly Thr Leu
                100                 105                 110
Val Thr Val Ser Ser Gly Gln Pro Lys Ala Pro Ser Val Phe Pro Leu
            115                 120                 125
Ala Pro Cys Cys Gly Asp Thr Pro Ser Ser Thr Val Thr Leu Gly Cys
130                 135                 140
Leu Val Lys Gly Tyr Leu Pro Glu Pro Val Thr Val Thr Trp Asn Ser
145                 150                 155                 160
Gly Thr Leu Thr Asn Gly Val Arg Thr Phe Pro Ser Val Arg Gln Ser
                165                 170                 175
Ser Gly Leu Tyr Ser Leu Ser Ser Val Val Ser Val Thr Ser Ser Ser
                180                 185                 190
Gln Pro Val Thr Cys Asn Val Ala His Pro Ala Thr Asn Thr Lys Val
            195                 200                 205
Asp Lys Thr Val Ala Pro Ser Thr Cys Ser Lys Pro Thr Cys Pro Pro
210                 215                 220
Pro Glu Leu Leu Gly Gly Pro Ser Val Phe Ile Phe Pro Lys Pro
225                 230                 235                 240
Lys Asp Thr Leu Met Ile Ser Arg Thr Pro Glu Val Thr Cys Val Val
                245                 250                 255
Val Asp Val Ser Gln Asp Asp Pro Glu Val Gln Phe Thr Trp Tyr Ile
            260                 265                 270
Asn Asn Glu Gln Val Arg Thr Ala Arg Pro Pro Leu Arg Glu Gln Gln
        275                 280                 285
```

```
Phe Asn Ser Thr Ile Arg Val Val Ser Thr Leu Pro Ile Ala His Gln
            290                 295                 300

Asp Trp Leu Arg Gly Lys Glu Phe Lys Cys Lys Val His Asn Lys Ala
305                 310                 315                 320

Leu Pro Ala Pro Ile Glu Lys Thr Ile Ser Lys Ala Arg Gly Gln Pro
                325                 330                 335

Leu Glu Pro Lys Val Tyr Thr Met Gly Pro Pro Arg Glu Glu Leu Ser
            340                 345                 350

Ser Arg Ser Val Ser Leu Thr Cys Met Ile Asn Gly Phe Tyr Pro Ser
            355                 360                 365

Asp Ile Ser Val Glu Trp Glu Lys Asn Gly Lys Ala Glu Asp Asn Tyr
        370                 375                 380

Lys Thr Thr Pro Ala Val Leu Asp Ser Asp Gly Ser Tyr Phe Leu Tyr
385                 390                 395                 400

Ser Lys Leu Ser Val Pro Thr Ser Glu Trp Gln Arg Gly Asp Val Phe
                405                 410                 415

Thr Cys Ser Val Met His Glu Ala Leu His Asn His Tyr Thr Gln Lys
                420                 425                 430

Ser Ile Ser Arg Ser Pro Gly Lys
            435                 440

<210> SEQ ID NO 10
<211> LENGTH: 214
<212> TYPE: PRT
<213> ORGANISM: artificial sequence
<220> FEATURE:
<223> OTHER INFORMATION: mature peptide: light chain
<220> FEATURE:
<221> NAME/KEY: DOMAIN
<222> LOCATION: (1)..(111)
<223> OTHER INFORMATION: vL

<400> SEQUENCE: 10

Leu Val Met Thr Gln Thr Pro Ala Ser Val Ser Ala Ala Val Gly Gly
1               5                   10                  15

Thr Val Thr Ile Ser Cys Gln Ala Ser Gln Ser Ile Thr Asp Gln Leu
            20                  25                  30

Ser Trp Tyr Gln His Gln Pro Gly Gln Pro Pro Lys Leu Leu Ile Tyr
        35                  40                  45

Arg Ala Ser Thr Leu Ala Ser Gly Val Pro Ser Arg Phe Ser Gly Ser
    50                  55                  60

Gly Ser Glu Thr Glu Phe Ser Leu Thr Ile Ser Gly Leu Gln Cys Ala
65                  70                  75                  80

Asp Ala Ala Thr Tyr Tyr Cys Leu Gly Val His Gly Tyr Ser Ser Asp
                85                  90                  95

Asp Ala Ile Ser Phe Gly Gly Gly Thr Glu Val Val Lys Gly Asp
                100                 105                 110

Pro Val Ala Pro Thr Val Leu Ile Phe Pro Pro Ala Ala Asp Gln Val
            115                 120                 125

Ala Thr Gly Thr Val Thr Ile Val Cys Val Ala Asn Lys Tyr Phe Pro
        130                 135                 140

Asp Val Thr Val Thr Trp Glu Val Asp Gly Thr Thr Gln Thr Thr Gly
145                 150                 155                 160

Ile Glu Asn Ser Lys Thr Pro Gln Asn Ser Ala Asp Cys Thr Tyr Asn
                165                 170                 175

Leu Ser Ser Thr Leu Thr Leu Thr Ser Thr Gln Tyr Asn Ser His Lys
```

```
            180                 185                 190
Glu Tyr Thr Cys Lys Val Thr Gln Gly Thr Thr Ser Val Val Gln Ser
        195                 200                 205
Phe Asn Arg Gly Asp Cys
        210

<210> SEQ ID NO 11
<211> LENGTH: 1380
<212> TYPE: DNA
<213> ORGANISM: artificial sequence
<220> FEATURE:
<223> OTHER INFORMATION: heavy chain

<400> SEQUENCE: 11
atggagactg ggctgcgctg gcttctcctg gtcgctgtgc tcaaaggtgt ccagtgtcag      60
gagcagctgg aggagtccgg gggagacctg gtcaagcctg ggcatccct gacactcacc     120 tgcacagcct ctggattctc cttcagtagc agcgcctgga tatgctgggt ccgccaggct    180
ccagggaagg ggctggagtg gatcgcatgc attttcactg gaaatagtga tatcaccatt    240
tacgcgaact gggcgaaagg ccgatccacc atctccagaa cctcgtcgac acggtgact    300 ctgcaagtga ccagtctgac agccgcggac acggccactt atttctgtgc gagaaattta    360
gctgctacta aattgtgggg ccccggcacc ctggtcaccg tctcctcagg caacctaag     420 gctccatcag tcttcccact ggcccccgc tgcggggaca cccagctc acggtgacc       480 ctgggctgcc tggtcaaagg gtacctcccg gagccagtga ccgtgacctg aactcgggc    540 accctcacca tggggtacg caccttcccg tccgtccggc agtcctcagg cctctactcg    600
ctgagcagcg tggtgagcgt gacctcaagc agccagcccg tcacctgcaa cgtggcccac    660
ccagccacca acaccaaagt ggacaagacc gttcgcgcct cgacatgcag caagcccacg    720
tgcccacccc ctgaactcct gggggggaccg tctgtcttca tcttcccccc aaaacccaag    780
gacaccctca tgatctcacg cacccccgag gtcacatgcg tggtggtgga cgtgagccag    840
gatgaccccg aggtgcagtt cacatggtac ataaacaacg agcaggtgcg caccgcccgg    900
ccgccgctac gggagcagca gttcaacagc acgatccgcg tggtcagcac cctccccatc    960
gcgcaccagg actggctgag gggcaaggag ttcaagtgca aagtccacaa caaggcactc   1020
ccggccccca tcgagaaaac catctccaaa gccagagggc agcccctgga gccgaaggtc   1080
tacaccatgg gccctccccg ggaggagctg agcagcaggt cggtcagcct gacctgcatg   1140
atcaacggct ctaccccttc cgacatctcg gtggagtggg agaagaacgg gaaggcagag   1200
gacaactaca agaccacgcc ggccgtgctg acagcgacg gctcctactt cctctacagc   1260
aagctctcag tgcccacgag tgagtggcag cggggcgacg tcttcacctg ctccgtgatg   1320
cacgaggcct gcacaaacca ctacacgcag aagtccatct cccgctctcc gggtaaatga   1380

<210> SEQ ID NO 12
<211> LENGTH: 714
<212> TYPE: DNA
<213> ORGANISM: artificial sequence
<220> FEATURE:
<223> OTHER INFORMATION: light chain

<400> SEQUENCE: 12
atggacacga gggcccccac tcagctgctg ggctcctgc tgctctggct cccaggtgcc      60
acatttgccc tggtgatgac ccagactcca gcctccgtgt ctgccgctgt gggaggcaca    120
gtcaccatca gttgccaggc cagtcagagc attaccgatc aactatcctg gtatcagcac    180
```

```
caaccagggc agcctcccaa gctcctgatc tacagggcat ccactctggc atctggggtc    240
ccatcgcggt tcagcggcag tggatctgag acagaattct ctctcaccat cagcggcttg    300
cagtgtgccg atgctgccac ttactactgt ctaggtgttc atggttatag tagtgatgat    360
gctatttctt tcggcggagg gaccgaggtg gtggtcaaag gtgatccagt tgcacctact    420
gtcctcatct tcccaccagc tgctgatcag gtggcaactg gaacagtcac catcgtgtgt    480
gtggcgaata atactttcc cgatgtcacc gtcacctggg aggtggatgg cacccaccaa     540
acaactggca tcgagaacag taaaacaccg cagaattctg cagattgtac ctacaacctc    600
agcagcactc tgacactgac cagcacacag tacaacagcc acaaagagta cacctgcaag    660
gtgacccagg gcacgacctc agtcgtccag agcttcaata ggggtgactg ttag          714
```

```
<210> SEQ ID NO 13
<211> LENGTH: 400
<212> TYPE: PRT
<213> ORGANISM: Artificial Sequence
<220> FEATURE:
<223> OTHER INFORMATION: Recombinant fusion protein consisting of human
      CD95 extracellular domain with human IgG1 FC-part to its
      C-terminus
<220> FEATURE:
<221> NAME/KEY: SIGNAL
<222> LOCATION: (1)..(16)
<223> OTHER INFORMATION: Variable cleavage sites
<220> FEATURE:
<221> NAME/KEY: SIGNAL
<222> LOCATION: (1)..(20)
<223> OTHER INFORMATION: Variable cleavage sites
<220> FEATURE:
<221> NAME/KEY: SIGNAL
<222> LOCATION: (1)..(25)
<223> OTHER INFORMATION: Variable cleavage sites
<220> FEATURE:
<221> NAME/KEY: DOMAIN
<222> LOCATION: (26)..(172)
<223> OTHER INFORMATION: Human CD95 extracellular domain
<220> FEATURE:
<221> NAME/KEY: MOD_RES
<222> LOCATION: (26)..(26)
<223> OTHER INFORMATION: PYRROLIDONE CARBOXYLIC ACID
<220> FEATURE:
<221> NAME/KEY: DISULFID
<222> LOCATION: (59)..(73)
<220> FEATURE:
<221> NAME/KEY: DISULFID
<222> LOCATION: (63)..(82)
<220> FEATURE:
<221> NAME/KEY: DISULFID
<222> LOCATION: (85)..(101)
<220> FEATURE:
<221> NAME/KEY: DISULFID
<222> LOCATION: (104)..(119)
<220> FEATURE:
<221> NAME/KEY: DISULFID
<222> LOCATION: (107)..(127)
<220> FEATURE:
<221> NAME/KEY: CARBOHYD
<222> LOCATION: (118)..(118)
<223> OTHER INFORMATION: N-linked Glycosylation at Position N118
<220> FEATURE:
<221> NAME/KEY: DISULFID
<222> LOCATION: (129)..(143)
<220> FEATURE:
<221> NAME/KEY: DISULFID
<222> LOCATION: (135)..(140)
<220> FEATURE:
<221> NAME/KEY: CARBOHYD
<222> LOCATION: (136)..(136)
<223> OTHER INFORMATION: N-linked Glycosylation at Position N136
<220> FEATURE:
<221> NAME/KEY: DISULFID
```

```
<222> LOCATION: (146)..(157)
<220> FEATURE:
<221> NAME/KEY: DISULFID
<222> LOCATION: (149)..(165)
<220> FEATURE:
<221> NAME/KEY: DOMAIN
<222> LOCATION: (172)..(400)
<223> OTHER INFORMATION: Human IgG1-FC domain (one amino acid overlap
      with CD95 domain)
<220> FEATURE:
<221> NAME/KEY: DISULFID
<222> LOCATION: (173)..(173)
<223> OTHER INFORMATION: Interchain cystine forming residue.
<220> FEATURE:
<221> NAME/KEY: DISULFID
<222> LOCATION: (179)..(179)
<223> OTHER INFORMATION: Interchain cystine forming residue.
<220> FEATURE:
<221> NAME/KEY: DISULFID
<222> LOCATION: (182)..(182)
<223> OTHER INFORMATION: Interchain cystine forming residue
<220> FEATURE:
<221> NAME/KEY: DISULFID
<222> LOCATION: (214)..(274)
<220> FEATURE:
<221> NAME/KEY: CARBOHYD
<222> LOCATION: (250)..(250)
<223> OTHER INFORMATION: N-linked Glycosylation at Position N250
<220> FEATURE:
<221> NAME/KEY: DISULFID
<222> LOCATION: (320)..(378)

<400> SEQUENCE: 13

Met Val Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Cys Asp Lys Thr
                165                 170                 175

His Thr Cys Pro Pro Cys Pro Ala Pro Glu Leu Leu Gly Gly Pro Ser
            180                 185                 190

Val Phe Leu Phe Pro Pro Lys Pro Lys Asp Thr Leu Met Ile Ser Arg
        195                 200                 205

Thr Pro Glu Val Thr Cys Val Val Val Asp Val Ser His Glu Asp Pro
    210                 215                 220

Glu Val Lys Phe Asn Trp Tyr Val Asp Gly Val Glu Val His Asn Ala
225                 230                 235                 240
```

```
Lys Thr Lys Pro Arg Glu Glu Gln Tyr Asn Ser Thr Tyr Arg Val Val
            245                 250                 255

Ser Val Leu Thr Val Leu His Gln Asp Trp Leu Asn Gly Lys Glu Tyr
        260                 265                 270

Lys Cys Lys Val Ser Asn Lys Ala Leu Pro Ala Pro Ile Glu Lys Thr
    275                 280                 285

Ile Ser Lys Ala Lys Gly Gln Pro Arg Glu Pro Gln Val Tyr Thr Leu
290                 295                 300

Pro Pro Ser Arg Glu Glu Met Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
            340                 345                 350

Ser Asp Gly Ser Phe Phe Leu Tyr Ser Lys Leu Thr Val Asp Lys Ser
        355                 360                 365

Arg Trp Gln Gln Gly Asn Val Phe Ser Cys Ser Val Met His Glu Ala
    370                 375                 380

Leu His Asn His Tyr Thr Gln Lys Ser Leu Ser Leu Ser Pro Gly Lys
385                 390                 395                 400

<210> SEQ ID NO 14
<211> LENGTH: 281
<212> TYPE: PRT
<213> ORGANISM: Homo sapiens
<220> FEATURE:
<221> NAME/KEY: MISC_FEATURE
<223> OTHER INFORMATION: human CD95L

<400> SEQUENCE: 14

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Pro Pro Leu Pro
50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205
```

```
His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
                260                 265                 270

Gln Thr Phe Phe Gly Leu Tyr Lys Leu
                275                 280

<210> SEQ ID NO 15
<211> LENGTH: 21
<212> TYPE: PRT
<213> ORGANISM: Artificial Sequence
<220> FEATURE:
<223> OTHER INFORMATION: CD95L_NT (1-21)

<400> SEQUENCE: 15

Met Gln Gln Pro Phe Asn Tyr Pro Tyr Pro Gln Ile Tyr Trp Val Asp
1               5                   10                  15

Ser Ser Ala Ser Ser
            20

<210> SEQ ID NO 16
<211> LENGTH: 10
<212> TYPE: PRT
<213> ORGANISM: Artificial Sequence
<220> FEATURE:
<223> OTHER INFORMATION: CD95L_NT (1-10)

<400> SEQUENCE: 16

Met Gln Gln Pro Phe Asn Tyr Pro Tyr Pro
1               5                   10

<210> SEQ ID NO 17
<211> LENGTH: 10
<212> TYPE: PRT
<213> ORGANISM: Artificial Sequence
<220> FEATURE:
<223> OTHER INFORMATION: CD95L_NT (5-14)

<400> SEQUENCE: 17

Phe Asn Tyr Pro Tyr Pro Gln Ile Tyr Trp
1               5                   10

<210> SEQ ID NO 18
<211> LENGTH: 11
<212> TYPE: PRT
<213> ORGANISM: Artificial Sequence
<220> FEATURE:
<223> OTHER INFORMATION: CD95L_NT (11-21)

<400> SEQUENCE: 18

Gln Ile Tyr Trp Val Asp Ser Ser Ala Ser Ser
1               5                   10

<210> SEQ ID NO 19
<211> LENGTH: 6
<212> TYPE: PRT
<213> ORGANISM: Artificial Sequence
<220> FEATURE:
<223> OTHER INFORMATION: CD95L_NT (13-18)
```

<400> SEQUENCE: 19

Tyr Trp Val Asp Ser Ser
1               5

<210> SEQ ID NO 20
<211> LENGTH: 7
<212> TYPE: PRT
<213> ORGANISM: Artificial Sequence
<220> FEATURE:
<223> OTHER INFORMATION: CD95L_NT (13-19)

<400> SEQUENCE: 20

Tyr Trp Val Asp Ser Ser Ala
1               5

<210> SEQ ID NO 21
<211> LENGTH: 6
<212> TYPE: PRT
<213> ORGANISM: Artificial Sequence
<220> FEATURE:
<223> OTHER INFORMATION: CD95L_NT (14-19)

<400> SEQUENCE: 21

Trp Val Asp Ser Ser Ala
1               5

<210> SEQ ID NO 22
<211> LENGTH: 10
<212> TYPE: PRT
<213> ORGANISM: Artificial Sequence
<220> FEATURE:
<223> OTHER INFORMATION: CD95L_NT (12-21)

<400> SEQUENCE: 22

Ile Tyr Trp Val Asp Ser Ser Ala Ser Ser
1               5                   10

<210> SEQ ID NO 23
<211> LENGTH: 10
<212> TYPE: PRT
<213> ORGANISM: Artificial Sequence
<220> FEATURE:
<223> OTHER INFORMATION: CD95L_NT (12-21 Y-S)

<400> SEQUENCE: 23

Ile Ser Trp Val Asp Ser Ser Ala Ser Ser
1               5                   10

<210> SEQ ID NO 24
<211> LENGTH: 10
<212> TYPE: PRT
<213> ORGANISM: Artificial Sequence
<220> FEATURE:
<223> OTHER INFORMATION: CD95L_NT (12-21 W-E)

<400> SEQUENCE: 24

Ile Tyr Phe Val Asp Ser Ser Ala Ser Ser
1               5                   10

<210> SEQ ID NO 25
<211> LENGTH: 10
<212> TYPE: PRT
<213> ORGANISM: Artificial Sequence
<220> FEATURE:
<223> OTHER INFORMATION: CD95L_NT (12-21 A-V)

<400> SEQUENCE: 25

```
Ile Tyr Trp Val Asp Ser Ser Val Ser Ser
1               5                   10
```

DIAGNOSTIC ANTI-CD95L ANTIBODY

This application is a continuation of PCT/EP2015/059354, filed Apr. 29, 2015; which claims priority to PCT/EP2014/058746, filed Apr. 29, 2014. The contents of the above applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence_Listing.txt with a creation date of Sep. 9, 2016, and a size of 20.4 kilobytes. The Sequence Listing filed via EFS-Web is part of the specification and is hereby incorporated in its entirety by reference herein.

DESCRIPTION

The present invention relates to a specific CD95L antibody and to the use thereof in the diagnosis of a cancer disease.

A particular aspect is an antibody specifically binding to CD95L, for use in diagnosing a cancer disease by classifying the cancer disease according the level of CD95L expression.

Yet another aspect is a method of prognosing the overall survival time or/and the relaps-free survival time in a cancer patient, said method comprising (a) determining CD95L expression in a cancer sample using a specific CD95L antibody, and (b) prognosing the survival time or/and the relaps-free survival time of the patient by the level of CD95L expression, wherein the CD95L expression is negatively correlated with the survival time.

Yet another aspect of the present invention is a method of treatment of a cancer, said method comprising
(a) determining the expression of CD95L in a cancer sample obtained from a patient using a specific CD95L antibody, and
(b) administrating a CD95L inhibitor if in step (a), expression of CD95L has been detected in the cancer sample.

Invasion of surrounding brain tissue by isolated tumor cells represents one of the main obstacles to an effective therapy of glioblastoma multiforme (GBM). Gliomas encompass the majority of tumors originating in the central nervous system (CNS). In adults, the most common tumors are high-grade neoplasms derived from astrocytes or oligodendrocytes. The World Health Organization classifies these malignant tumors according to their degree of anaplasia into grade II (diffuse astrocytoma), grade III (anaplastic astrocytoma) and grade IV (GBM) (Kleihues, P., Burger, P. C., & Scheithauer, B. W. The new WHO classification of brain tumors *Brain Pathol.* 3, 255-268, 1993). Gliomas account for more than 50% of all brain tumors and are by far the most common primary brain tumors in adults. Despite, development of new diagnostic technologies, the survivalrate is extremely low. Only 3% are still alive five years after diagnosis. The clinical outcome of malignant gliomas depends on the invasion of isolated tumor cells in the normal brain tissue. Migrating cells can escape the surgical ablation of the tumor and are then the prime targets of post-surgical radiotherapy and adjuvant chemotherapy. Chemotherapeutic agents and irradiation act primarily by inducing apoptosis. This induction of apoptosis often involves activation of the CD95 (Apo-1/Fas) death receptor/ligand system. Nevertheless, most malignant glioma cells are resistant to CD95-induced apoptosis.

It was found previously that the expression of CD95L in the cancer samples is associated with a reduced survival of the patients. This means that CD95L expression is a prognostic factor of the overall survival time of a cancer patient. Example 1 demonstrates in a clinical phase II study that in tumor samples having the diagnosis "glioblastoma", CD95L is expressed to a variable extent.

Furthermore, Example 1 demonstrates that a CD95L inhibitor, for example APG101, can improve the survival of cancer in patients suffering from a cancer expressing CD95L. In contrast, patients suffering from a cancer which does not express CD95L, do not benefit from the treatment with a CD95L inhibitor. Example 1 enables a therapeutic strategy including a diagnostic step comprising determining the CD95L expression in a cancer sample, and then treating the patient with a CD95L inhibitor if CD95L is expressed. A diagnostic differentiation of cancer by expression of CD95L is enabled. This leads to a new diagnostic classification of cancer, for example glioblastoma, by the extent of CD95L expression, leading to an adapted therapy of those patients suffering from a cancer expressing CD95L. This strategy is advantageous, because the CD95L inhibitor is administered to those patients only in which a therapeutic success can be expected. This is disadvantageous in patients suffering from a cancer not expressing CD95L, because these patients will probably not benefit from a treatment with a CD95L inhibitor.

Current antibodies used for IHC based detection of CD95L are not suited for specific detection of CD95L (Sträter, 1991.). As CD95L is cleaved from the surface of the expressing cells a detection of CD95L using antibodies recognizing an extracellular epitope of CD95L (e.g. antibody "Clone G247-4" from BD Pharmingen, Catalog No. 556387) is not recommended as only partial amounts of total CD95L is detected. For this reason CD95L detection has to be based on the intracellular part of CD95L.

An additional difficulty is that current antibodies used for detection of CD95L are of polyclonal nature, e.g., polyclonal rabbit antibody anti Fas Ligand (FasL, CD95L, CD178) from Dianova catalogue number DLN-14047. Polyclonal antibodies are based on their limited batch size and the inevitable occurrence of variable batch to batch specificities, not suited to ensure a continuous specific detection of CD95L in an IHC-based analysis.

The problem of the present invention can be seen in the improvement of cancer diagnosis and therapy. The solution provided herein includes a specific anti-CD95L antibody and the use thereof in the diagnosis of a cancer disease, in particular for the diagnostic differentiation of cancer into a sub-type expressing CD95L, and a sub-type which does not express CD95L. These sub-types require a specific therapy based upon the CD95L expression. The solution provided in the present invention includes a specific therapy based upon the diagnosis of the sub-types identified in the present invention.

Surprisingly, the present invention identified a monoclonal antibody circumventing aforementioned limitations as it recognizes a linear intracellular epitope on CD95L in a highly specific manner as exemplified in FIGS. 9 and 10. This intracellular epitope has been shown to be unique for its suitability to detect CD95L in an IHC-based analysis as shown in FIGS. 6 and 7.

Thus, a first aspect of the invention is an anti-CD95L antibody specifically binding to an epitope comprising amino acids 13-19 of human CD95L. The amino acid sequence of human CD95L is shown in SEQ ID NO: 14.

The term "antibody" particularly refers to molecules comprising at least one immunoglobulin heavy chain and at least one immunoglobulin light chain. Each heavy and light chain may comprise a variable and a constant domain. The antigen binding site may be formed from the variable domains of a heavy chain and a light chain. A variable region (also referred to as variable domain) comprises complementarity determining regions (CDRs), e.g., a CDR1, a CDR2 and a CDR3 region and framework regions (FRs) flanking the CDRs.

The term "complementarity determining region" is readily understood by the skilled person (see, e.g., Harlow and Lane (EDS.), Antibodies: A Laboratory Manual, CSHL Press, Cold Spring Harbour, N.Y., 1988) and refers to the stretches of amino acids within the variable domain of an antibody that primarily make contact with the antigen and determine antibody specificity. This region is also known as the hypervariable region.

The present invention encompasses both full length immunoglobulin and functional immunoglobulin fragments like Fab, Fab', F(ab')2 fragments, Fv fragments, diabodies, single-chain antibody molecules and single-domain antibodies. Also other fragments are included as long as they exhibit the desired capability of binding to an epitope comprising amino acids 13-19 of human CD95L. For a review of certain antibody fragments, see Hudson et al., Nat. Met. 9: 129-134 (2003).

Diabodies are antibody fragments with two antigen-binding sites that may be bivalent or bispecific (see, e.g., Hudson et al., 2003). Single-chain antibodies are antibody fragments comprising all or a portion of the heavy chain variable domain, or all or a portion of the light chain variable domain of an antibody. Antibody fragments can be made by various techniques, including but not limited to proteolytic digestion of an intact antibody as well as production by recombinant hosts (e.g., *E-coli* or phage) as described herein.

Also encompassed by the present invention are human antibodies. The term "human antibody" is meant to encompass any fully human or humanized antibodies. Human antibodies may be prepared from genetically engineered animals, e.g., animals comprising a xenogeneic immune system or from antibody display libraries according to known techniques. Human antibodies are described generally in Van Dijk and Van De Winkel (Car. Opin. Pharmacol. 5: 368-74 (2001)) and Lonberg (Car. Opin. Immunol. 20: 450-459 (2008)).

Humanized antibodies may be prepared by humanization of monoclonal antibodies according to known techniques. Typically, a non-human antibody is humanized to reduce immunogenicity to humans, while retaining the specificity and affinity of the parental non-human antibody. Humanized antibodies and methods of making them are reviews, e.g. in *Alamargo and Fransson, Front. Biosci.* 13: 1619-1633 (2008).

The antibodies of the present invention are characterized in that they specifically bind to an epitope comprising amino acids 13-19 of human CD95L. This intracellular epitope has been shown to be unique for its suitability to detect CD95L, in particular in an IHC-based analysis.

The term "bind" or "binding" of an antibody means an at least temporary interaction or association with or to a target antigen, i.e. human CD95L comprising fragments thereof containing an epitope.

In certain embodiments, an antibody provided herein has a dissociation constant (Kd) of $\leq 1$ μM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g. $10^{-9}$ M to $10^{13}$M).

In one embodiment, Kd is measured by a radio-labeled antigen binding assay (Radioimmunoassay, RIA) performed with the Fab version of an antibody of interest and its antigen.

According to another embodiment, Kd is measured using surface plasmon resonance assays with immobilized antigen. According to a preferred embodiment of the present invention, the antibodies are human monoclonal antibodies directed against an epitope of human CD95L as described herein.

The antibodies of the invention may be of various immunoglobulin (Ig) types, for example of the IgA-, IgD-, IgE-, IgG- or IgM-type, preferably of the IgG- or IgM-type including but not limited to the IgG1-, IgG2-, IgG3-, IgG4-, IgM1 and IgM2-type. In one preferred embodiment the antibody is of the IgG1type.

Preferably, the antibodies of the invention are monoclonal antibodies.

In certain embodiments of the present invention, the antibody may comprise specific heavy chain complementarity determining regions CDRH1, CDRH2 and/or CDRH3 as described herein below.

In one embodiment, the antibody comprises a heavy chain comprising:

a heavy chain complementarity determining region 1 (CDRH1) having the amino acid sequence as shown in SEQ ID NO: 1 or an amino acid sequence differing in 1 or 2 amino acids therefrom, a heavy chain complementarity determining region 2 (CDRH2) having the amino acid sequence as shown in SEQ ID NO: 2 or an amino acid sequence differing in 1 or 2 amino acids therefrom, and/or a heavy chain complementarity determining region 3 (CDRH3) having the amino acid sequence as shown in SEQ ID NO: 3 or an amino acid sequence differing in 1 or 2 amino acids therefrom.

The antibody according to the invention may also comprise specific light chain complementarity determining regions CDRL1, CDRL2 and/or CDRL3. Accordingly, in one embodiment, the antibody comprises a light chain comprising:

a light chain complementarity determining region 1 (CDRL1) having the amino acid sequence as shown in SEQ ID NO: 4, or an amino acid sequence differing in 1 or 2 amino acids therefrom, a light chain complementarity determining region 2 (CDRL2) having the amino acid sequence as shown in SEQ ID NO: 5, or an amino acid sequence differing in 1 or 2 amino acids therefrom, and/or a light chain complementary determining region 3 (CDRL3) having the amino acid sequence as shown in SEQ ID NO: 6, or an amino acid sequence differing in 1 or 2 amino acids therefrom.

In a preferred embodiment, the antibody comprises a specific combination of CDRs within one heavy chain and/or within one light chain. Accordingly, a particularly preferred antibody of the present invention comprises a heavy chain including a CDRH1 as shown in SEQ ID NO: 1, or an amino acid sequence differing in 1 or 2 amino acids therefrom, a CDRH2 as shown in SEQ ID NO: 2, or an amino acid sequence differing in 1 or 2 amino acids therefrom, and a CDRH3 as shown in SEQ ID NO: 3, or an amino acid sequence differing in 1 or 2 amino acids therefrom, and a light chain including a CDRL1 as shown in SEQ ID NO: 4, or an amino acid sequence differing in 1 or 2 amino acids therefrom, a CDRL2 as shown in SEQ ID NO: 5, or an amino acid sequence differing in 1 or 2 amino acids therefrom, and a CDRL3 as shown in SEQ ID NO: 6, or an amino acid sequence differing in 1 or 2 amino acids therefrom.

Preferably, the CDR sequences are those shown in SEQ ID NOs: 1-6 without any variation.

In a preferred embodiment of the invention, the anti-CD95L antibody comprises a heavy chain variable region (VH) as shown in SEQ ID NO: 7 or a sequence having a sequence identity of at least 90% over the whole heavy chain variable region, preferably at least 95% sequence identity. Furthermore, the antibody of the invention preferably comprises a light chain variable region (VL) as shown in SEQ ID NO: 8 or a sequence having a sequence identity of at least 90% over the whole light chain variable region, preferably at least 95% sequence identity. Particularly preferred are antibodies comprising a heavy chain variable region as shown in SEQ ID NO: 7 and a light chain variable region as shown in SEQ ID NO: 8.

According to a particularly preferred embodiment of the invention, the antibody of the invention comprises a heavy chain comprising the amino acid sequence as shown in SEQ ID NO: 9, or an amino acid sequence having a sequence identity of at least 90% thereto over the whole heavy chain amino acid sequence, and a light chain comprising an amino acid sequence as shown in SEQ ID NO: 10, or an amino acid sequence having a sequence identity of at least 90% thereto over the whole length of the light chain amino acid sequence. The sequence identity of the heavy chain and the light chain amino acid sequence is preferably at least 95% to the sequences shown in SEQ ID NO: 9 and 10. Most preferred is an antibody comprising the heavy chain amino acid sequence as shown in SEQ ID NO: 9 and the light chain amino acid sequence as shown in SEQ ID NO: 10.

To determine the epitope on human CD95L recognized by the antibody, chemically prepared arrays of protein sequence derived short peptides derived from the amino acid sequence of human CD95L can be used to locate and identify antibody epitopes (Reinike W., Methods Mol. Biol., 2004, 248: 443-63). A further method to map the epitopes in human CD95L bound by the antibodies of the invention comprises Snaps/SELDI (Wang et al., Int. J. Cancer, 2001, Jun. 15, 92(6): 871-6) or a routine cross-blocking assay such as described in *Antibodies, A Laboratory Manual*, Cold Spring Harbor Laboratory, Ed Harlow and David Lane (1988) can be performed.

As mentioned above, the antibodies of the invention show advantageous properties with respect to their binding specificity and biological activity, in particular with respect to their capability to recognize epitopes of CD95L.

The antibodies of the present invention may be coupled to a heterologous group, e.g., a label or an effector group. An antibody conjugate comprising an antibody of the invention coupled to a label group, is particularly suitable for diagnostic applications. As used herein, the term "label group" refers to a detectable marker, e.g., a radiolabelled amino acid or biotin moiety, a fluorescent marker, an enzyme or any other type of marker which is known in the art.

The invention also relates to a nucleic acid molecule encoding the antibody as disclosed above. The term "nucleic acid molecule" encompasses DNA, e.g., single- or double-stranded DNA or RNA. The DNA may be of genomic, cDNA or synthetic origin, or a combination thereof. The nucleic acid molecule of the invention may be in operative linkage to an expression control sequence, i.e. to a sequence which is necessary to effect the expression of coding nucleic acid sequences. Such expression control sequences may include promoters, enhancers, ribosomal binding sites and/or transcription termination sequences. Specific examples of suitable expression control sequences are known in the art.

According to a preferred embodiment, the invention is directed to an isolated nucleic acid molecule comprising a nucleic acid sequence selected from the group consisting of
(a) a nucleic acid sequence encoding an antibody, or a functional fragment thereof as defined above,
(b) a nucleic acid sequence complementary to any one of the sequences in (a), and
(c) a nucleic acid sequence capable of hybridizing to (a) or (b) under stringent conditions.

According to a particularly preferred embodiment of the invention, a nucleic acid molecule comprises a sequence encoding the variable region of the heavy chain and a sequence encoding the variable region of the light chain of the antibody. In an alternative embodiment, a combination of two nucleic acid molecules is provided, wherein one nucleic acid molecule encodes the light chain of the antibody and the other nucleic acid molecule encodes the heavy chain of the antibody. A preferred nucleic acid molecule of the invention is an isolated nucleic acid molecule comprising a nucleic acid sequence as shown in SEQ ID NO: 11 and/or 12.

The term "hybridizing under stringent conditions" means that two nucleic acid fragments hybridize with one another under standardized hybridization conditions as described, for example in Sambrook et al., "*Expression of cloned Genes in E. coli*" in *Molecular Cloning: A Laboratory Manual* (1989), Cold Spring Harbor Laboratory Press, New York, USA. Such conditions are, for example, hybridization in 6.0×SSC (Saline Sodium Citrate) at about 45° C. followed by a washing step with 2.0×SSC at 50° C., preferably 2.0×SSC at 65° C. or 0.2×SSC at 50° C., preferably 0.2×SSC at 65° C.

The nucleic acid molecule of the invention may be located on a vector which may additionally contain a replication origin and/or a selection marker gene. Examples of vectors are e.g. plasmids, cosmids, phages, viruses etc. Thus, a further embodiment of the invention is a vector comprising a nucleic acid sequence as disclosed herein. Preferably, the vector is an expression vector. Said vector may, for example, be a phage, plasmid, viral or retro viral vector. Retro viral vectors may be replication competent or replication defective. In the latter case, viral propagation generally will occur only in complementing hosts/cells.

The nucleic acid molecules of the invention may be joined to a vector containing selectable markers for propagation in a host. Generally, a plasmid vector is introduced in a precipitate such as a calcium phosphate precipitate or rubidium chloride precipitate or in a complex with a charged lipid or in carbon-based clusters such as fullerenes. Should the vector be a virus, it may be packed in vitro using an appropriate packaging cell line prior to application to host cells.

Preferably, the vector of the invention is an expression vector, wherein the nucleic acid molecule is operatively linked to one or more control sequences allowing the transcription and optionally expression in prokaryotic and/or eukaryotic host cells. Expression of said nucleic acid molecule comprises transcription of the nucleic acid molecule, preferably into a translatable mRNA. Regulatory elements ensuring expression in eukaryotic cells, preferably mammalian cells, are well-known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers. Possible regulatory elements permitting expression in prokaryotic host cells comprise, e.g. the lac, trp or tac promoter in *E. coli*, and examples for regulatory elements permitting expression in eukaryotic host cells are the AOXI or GAL-1 promoter in yeast or the CMV (Cytomegalovirus)-, SV40 (Simian Virus 40)-, RSV-promoter (Rous sarcoma virus), CMV-enhancer, SV40-enhancer or a globin intron in mammalian and other animal cells. Beside elements which are responsible for the initiation of transcription, such regulatory elements may also comprise transcription termination signals such as the SV40-poly-A site or the tk-poly-A site, downstream of the polynucleotide. In this context, suitable expression vectors are known in the art such as Okayama-Berg cDNA expression vector pcDV1 (Pharmacia), pCDM8, pRc/CMV, pcDNA1, pcDNA3 or pSPORTI (Thermo Fisher Scientific). Preferably, said vector is an expression vector and/or a gene transfer or targeting vector. Expression vectors derived from viruses such as retrovirus, vaccina virus, adeno-associated virus, herpes virus or bovine papilloma virus may be used for delivery of the polynucleotides or vector of the invention into targeted cell population. Methods which are well-known to those skilled in the art can be used to construct recombinant viral vectors; see for example the techniques described in Sambrook, *Molecular Cloning, A Laboratory Manual*, Cold Spring Harbor Laboratory Press (2001, 3$^{rd}$ edition), N.Y. and Ausubel, *Current Protocols in Molecular Biology*, Green Publishing Associates and Wiley Interscience, N.Y. (1994). Alternatively, the nucleic acid molecules of the invention can be reconstituted into liposomes for delivery to target cells.

Further, the invention refers to a host which comprises the nucleic acid molecule or the vector as described above. The nucleic acid molecule or the vector may be introduced into the host by transformation, transfection or transduction according to any method known in the art.

Said host may be a prokaryotic or eukaryotic cell or a non-human transgenic animal. The polynucleotide or vector of the invention which is present in the host may either be integrated into the genome of the host or it may be maintained extrachromosomally. In this respect, it is also to be understood that the nucleic acid molecule of the invention can be used for "gene targeting" and/or "gene replacement", for restoring a mutant gene or for creating a mutant gene via homologous recombination; see for example Mouellic, *Proc. Natl. Acad. Sci. USA*, 87 (1990), 4712-4716; Joyner, *Gene Targeting, A Practical Approach*, Oxford University Press.

The host can be any prokaryotic or eukaryotic cell such as a bacterial, insect, fungal, plant, animal, mammalian or preferably a human cell. Preferred fungal cells are, for example those of the genus *Saccharomyces*, in particular those of the species *S. cerevisiae*. The term "prokaryotic" is meant to include all bacteria which can be transformed or transfected with a polynucleotide for the expression of a variant polypeptide of the invention. Prokaryotic hosts may include gram negative as well as gram positive bacteria such as for example *E. coli, Salmonella typhimurium, Serratia marcescens* and *Bacillus subtilis*. A polynucleotide coding for a mutant form of variant polypeptides of the invention can be used to transform or transfect the host using any of the techniques commonly known to those of ordinary skill in the art. Methods for preparing fused operably linked genes and expression them in bacteria or animal cells are well-known in the art (Sambrook, *Molecular Cloning, A Laboratory Manual*, Cold Spring Harbor Laboratory Press (2001, 3$^{rd}$ edition). The genetic constructs and methods described therein can be utilized for expression of variant antibodies, antibody fragments or derivatives thereof of the invention in e.g. prokaryotic hosts. In general, expression vectors containing promoter sequences, which facilitate the efficient transcription of the inserted nucleic acid molecule, are used in connection with the host. The expression vector typically contains an origin of replication, a promoter and a terminator as well as specific genes which are capable of providing phenotypic selection of the transformed cells. The transformed prokaryotic hosts can be grown in fermentors and cultured according to techniques known in the art to achieve optimal cell growth. The antibodies, antibody fragments or derivatives thereof of the invention can then be isolated from the growth medium, cellular lysates or cellular membrane fractions. The isolation and purification of the microbial or otherwise expressed antibodies, antibody fragments or derivatives thereof of the invention may be by any conventional means, such as for example preparative chromatographic separations and immunological separations such as those involving the use of monoclonal or polyclonal antibodies.

According to one embodiment of the invention, the host is a human, bacteria, animal, fungal, amphibian or plant cell. Preferred animal cells include but are not limited to Chinese hamster ovary (CHO) cells, baby hamster kidney (BHK) cells, monkey kidney cells (COS), mouse embryonic fibroblast cells (NIH-3T3) and a number of other cell lines, including human cells.

In a particularly preferred embodiment, said animal cell is a rabbit cell. Preferred insect cells include but are not limited to cells from the SF9 cell lines.

The antibody of the invention may be prepared by a method, wherein said antibody is obtained from a host as described herein above. Thus, a further embodiment of the present invention is a method for the preparation of an antibody comprising culturing the host of the invention under conditions that allow synthesis of said antibody and recovering said antibody from said culture.

The transformed hosts can be grown in fermenters and cultured according to techniques known in the art to achieve optimal cell growth. Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like; see Scopes, *"Protein Purification"*, Springer-Verlag, N.Y. (1982). The antibody or its corresponding immunoglobulin chain(s) of the invention can then be isolated from the growth medium, cellular lysates or cellular membrane fractions. The isolation and purification of the e.g. microbially expressed antibodies or immunoglobulin chains of the invention may be by any conventional means, such as for example preparative chromatographic separations and immunological separations such as those involving the use of monoclonal or polyclonal antibodies directed e.g. against the constant region of the antibody of the invention.

It will be apparent to those skilled in the art that the antibodies of the invention can be further coupled to other moieties, e.g. drug targeting and imaging applications. Such coupling may be conducted chemically after expression of the antibody or antigen to side of attachment or the coupling product may be engineered into the antibody or antigen of the invention at the DNA level. The DNAs are then expressed in a suitable host system, and the expressed proteins are collected and renatured if necessary.

According to one embodiment, a recombinant cell as described above is cultured under conditions which allow expression of the antibody encoding nucleic acid molecules. The antibody may be collected from the cultured cell or the culture supernatant. Preferably, the antibody is prepared from a mammalian, particularly from a human cell.

Still a further aspect of the present invention relates to a pharmaceutical composition comprising the antibody as described above, optionally together with a pharmaceutically acceptable carrier. According to the invention, the pharmaceutical composition is adapted for a diagnostic use.

The term "carrier" includes agents, e.g. diluents, stabilizers, adjuvants or other types of excipients. Examples of pharmaceutically acceptable carriers are well-known in the art and include phosphate-buffered saline solutions, water, emulsions such as oil/water emulsions, various types of wetting agents, sterile solutions, etc. The pharmaceutical composition may be formulated by well-known conventional methods, i.e. by mixing the active agent with carriers and optionally other agents that are usually incorporated into the formulation.

A further aspect of the present invention is a method for diagnosing a cancer disease, comprising
(a) determining the expression of CD95L in a cancer sample using the above disclosed anti-CD95L antibody, and
(b) classifying the cancer disease according the level of CD95L expression.

In a preferred embodiment of the present invention the method for diagnosing a cancer disease may include a step (c), i.e. determining and/or selecting a method of treatment which is suitable for the type of cancer that has been diagnosed and/or carrying out the treatment.

In the present invention, expression of CD95L is determined by any known suitable method, but using the antibody of the present invention. For example, the determination may comprise a histological, histochemical or/and immunohistochemical (IHC) method using the above-described anti-CD95L antibody. Immunohistochemical methods are particularly preferred. According to the invention, it was surprisingly found that the antibodies of the invention are particularly suitable for use in immunohistochemical assays for determining CD95L.

The sample employed in the diagnosis of cancer as described herein can be an archived tumor tissue, for example a biopsy or surgery material embedded in paraffin, which has been obtained in an earlier stage of the disease.

The cancer disease can be classified by the level of CD95L expression into a CD95L positive cancer disease or a CD95L negative cancer disease.

In particular the CD95L positive cancer disease is characterised by a cell expressing CD95L on the cell surface. However, the methods described herein may also be based on the detection of intracellular epitopes of CD95L.

A cancer can be regarded as CD95L positive, if at least 1%, at least 2%, at least 5%, at least 10%, at least 20%, or at least 50% of the cells in a cancer sample express CD95L. The number of CD95L positive cells can be determined by counting the cells in a microscopic section.

CD95L expression is considered to be absent (CD95L negative) if essentially no cells expressing CD95L can be detected in the tissue sample, or if the sample is a sample which does not fulfil the criteria defined herein for a CD95L positive sample (non-positive sample). In a CD95L negative sample, the number of tumor cells expressing CD95L can be below the threshold defined herein for CD95L positive samples, for example below 1%, below 2%, below 3%, below 4%, below 5%, or below 10% of tumor cells.

CD95L expression in cells can be determined by immunohistochemical methods, such as the method disclosed in Example 2. In particular the expression of CD95L in the cancer sample is determined by contacting the sample with an above-disclosed anti-CD95L antibody specifically binding to amino acids 13-19 of human CD95L. The generation of an antibody of the invention is given in Example 7. Such anti-CD95L-specific antibodies or CD95L-recognising fragments thereof bind to an epitope comprising amino acids 13-19 of human CD95L (see FIG. 9).

It is particularly preferred that the antibodies according to the present invention are monoclonal antibodies.

Suitable labelling and staining methods are known. An example of staining with a streptavidin-coupled alkaline phosphatase binding to a biotinylated secondary antibody is given in Example 2.

A cancer can also be regarded as CD95L positive, if CD95L can be detected on at least 1%, at least 2%, at least 5%, at least 10%, at least 20%, or at least 50% of the area of tumor tissue in a tissue section. This value is termed herein as "% CD95L positive area of tumor tissue". Non-tumor tissue is excluded in this analysis. A tissue section can be prepared by known methods. Suitable methods for detection of CD95L are described herein. An exemplary method is described in Example 2. An example of determination of the area of CD95L positive tumor tissue is given in Example 3. CD95L expression can be considered to be absent (CD95L negative) if essentially no CD95L can be detected in the tissue sample, or if the value of % CD95L positive area of tumor tissue is below the threshold defined for a CD95 positive sample, for example below 1%, below 2%, below 3%, below 4%, below 5%, or below 10% of tumor area.

CD95L expression (e.g. in terms of cell number or surface in a tissue section) can be determined by known methods, for example by methods based upon automatized analysis of tissue sections.

By the method of the present invention, any type of cancer, in particular solid tumor tissue, can be diagnosed for expression of CD95L. The cancer to be diagnosed or/and treated may also be a cancer of lymphoid or myeloid origin.

Diagnosis based upon the expression of CD95L is of particular importance for diagnosis and treatment of those cancer types which include CD95L expression sub-types, and thus require a specific therapy adapted to the diagnosed CD95L expression sub-type. An example of CD95L expression sub-types of glioblastoma identified in the present invention is CD95L positive glioblastoma and CD95L negative glioblastoma, as described herein. The solution provided herein includes a specific therapy based upon the diagnosis of the CD95L expression sub-types identified in the present invention.

Any type of cancer, in particular solid tumor tissue, can be determined to be CD95L expression positive or CD95L expression negative. The cancer can be characterised by invasive growth. The cancer disease to be diagnosed according to the present invention as CD95L positive cancer or CD95L negative cancer can be selected from the group consisting of brain cancer, colon cancer, colorectal cancer, pancreatic cancer, breast cancer, lung cancer, renal cancer, liver cancer or/and metastatic disease thereof. In particular, the cancer disease is glioma, more particular glioblastoma.

For example, according to the present invention, the diagnosis brain tumor by hitherto known diagnostic methods can be specified to be a CD95L positive brain tumor or a CD95L negative brain tumor, based upon the outcome of determination of CD95L expression in a tumor sample, as described herein. Such known diagnostic methods include known histological or histopathological methods such as known methods of tissue staining and known immunohistochemical methods.

According to the present invention, the diagnosis glioma obtained by hitherto known diagnostic methods can be specified to be a CD95L positive glioma or a CD95L negative glioma.

According to the present invention, the diagnosis glioblastoma obtained by hitherto known diagnostic methods can be specified to be a CD95L positive glioblastoma or a CD95L negative glioblastoma.

According to the present invention, the diagnosis colorectal cancer obtained by hitherto known diagnostic methods can be specified to be a CD95L positive colorectal cancer or a CD95L negative colorectal cancer.

According to the present invention, the diagnosis pancreatic cancer obtained by hitherto known diagnostic methods can be specified to be a CD95L positive pancreatic cancer or a CD95L negative pancreatic cancer.

According to the present invention, the diagnosis colon cancer obtained by hitherto known diagnostic methods can be specified to be a CD95L positive colon cancer or a CD95L negative colon cancer.

According to the present invention, the diagnosis breast cancer obtained by hitherto known diagnostic methods can be specified to be a CD95L positive breast cancer or a CD95L negative breast cancer.

According to the present invention, the diagnosis lung cancer obtained by hitherto known diagnostic methods can be specified to be a CD95L positive lung cancer or a CD95L negative lung cancer.

According to the present invention, the diagnosis renal cancer obtained by hitherto known diagnostic methods can be specified to be a CD95L positive renal cancer or a CD95L negative renal cancer.

According to the present invention, the diagnosis liver cancer obtained by hitherto known diagnostic methods can be specified to be a CD95L positive liver cancer or a CD95L negative liver cancer.

According to the present invention, a metastatic disease caused by a specific type of cancer, as described herein, can be specified to be a CD95L positive metastatic disease or a CD95L negative metastatic disease.

Yet another aspect of the present invention is a monoclonal antibody of the invention specifically binding to amino acids 13-19 of human CD95L, for use in diagnosing a cancer disease by classifying the cancer disease according the level of CD95L expression. In this aspect, the cancer disease can be classified by the level of CD95L expression into a CD95L positive cancer disease or a CD95L negative cancer disease. The level of CD95L expression is preferably determined in an immunohistochemcial method using the antibody of the invention.

In this aspect, the cancer can be any cancer, as described herein. In particular, the cancer disease is selected from the group consisting of brain cancer, colon cancer, colorectal cancer, pancreatic cancer, breast cancer, lung cancer, renal cancer, liver cancer or/and metastatic disease thereof. More particular, the cancer disease is glioma, most particular glioblastoma.

Another aspect of the present invention is an anti-CD95L antibody of the invention specifically binding to amino acids 13-19 of human CD95L, for use in prognosing the overall survival time or/and the relaps-free survival time in a cancer patient, by classifying the cancer disease of the patient by the level of CD95L expression. The level of CD95L expression is preferably determined in an immunohistochemcial method using the antibody of the invention.

In this aspect, the cancer can be any cancer, as described herein. In particular, the cancer disease is selected from the group consisting of brain cancer, colon cancer, colorectal cancer, pancreatic cancer, breast cancer, lung cancer, renal cancer, liver cancer or/and metastatic disease thereof. More particular, the cancer disease is glioma, most particular glioblastoma.

In the present invention, the overall survival time (OS) denotes the chances of staying alive for a group of individuals suffering from a cancer. It denotes the percentage of individuals in the group who are likely to be alive after a particular duration of time.

Yet another aspect of the present invention is a method of prognosing the overall survival time or/and the relapse-free survival time in a cancer patient, said method comprising
(a) determining CD95L expression in a cancer sample using an antibody of the invention, and
(b) prognosing the survival time or/and the relapse-free survival time of the patient by the level of CD95L expression, wherein the CD95L expression is negatively correlated with the survival time of the patient.

In this aspect of the present invention, the cancer sample can be obtained from the patient. Preferably, the method does not include the step of obtaining the cancer sample from the patient.

In this aspect, the cancer disease can be classified by the level of CD95L expression into a CD95L positive cancer disease or a CD95L negative cancer disease. The level of CD95L expression is preferably determined in an immunohistochemcial method using the antibody of the invention.

In this aspect, the cancer can be any cancer, as described herein. In particular, the cancer disease is selected from the group consisting of brain cancer, colon cancer, colorectal cancer, pancreatic cancer, breast cancer, lung cancer, renal cancer, liver cancer or/and metastatic disease thereof. More particular, the cancer disease is glioma, most particular glioblastoma.

A further aspect of the present invention is a method of treatment of cancer, said method comprising
(a) determining the expression of CD95L in a cancer sample obtained from a patient using an anti-CD95L antibody of the present invention, and
(b) administrating a CD95L inhibitor if in step (a), expression of CD95L has been detected in the cancer sample.

Expression of CD95L is preferably determined in an immunohistochemcial method using the antibody of the present invention.

The cancer patient to be diagnosed or/and treated as described herein can be a patient with first or second relapse or progression of cancer, for example of glioblastoma. The patient may be a patient wherein standard treatment including radiotherapy (e.g. 60Gy) or/and temozolomide has failed, for example in the treatment of glioblastoma. In particular the patient is a candidate for re-irradiation, for example for treatment of glioblastoma.

In the therapeutic uses as described herein, the CD95L inhibitor can be administered systemically, for example by infusion or injection.

The CD95L inhibitor for therapeutic use according to the present invention can be any CD95L inhibitor known in the prior art. For example, the CD95L inhibitor can comprise a fusion protein comprising at least an extracellular CD95 domain or a functional fragment thereof and at least a Fc domain or functional fragment thereof. In particular, the fusion protein is selected from APG101, polypeptides having at least 70% identity to APG101 and functional fragments of APG101. As defined by SEQ ID NO: 13, APG101 can be a fusion protein comprising a human extracellular CD95 domain (amino acids 26-172) and a human IgG1 Fc domain (amino acids 172-400), further optionally comprising an N-terminal signal sequence (e.g. amino acids 1-25 of SEQ ID NO: 13). The presence of the signal peptide indicates the immature form of APG101. During maturation, the signal peptide is cleaved off. According to an especially preferred embodiment the signal sequence is cleaved off. APG101 with the signal sequence being cleaved off is also comprised by the term "unmodified APG101". In a further embodiment the fusion protein is a polypeptide having at least 70% identity, more preferably 75% identity, 80% identity, 85% identity, 90% identity, 95% identity, 96% identity, 97% identity, 98% identity, 99% identity with APG101. According to the present application the term "identity" relates to the extent to which two amino acid sequences being compared are invariant, in other words share the same amino acids in the same position.

The invention is further illustrated by the following Figures and Examples.

BRIEF DESCRIPTION OF THE DRAWINGS

This application contains at least one drawings executed in color. Copies of this patent or patent application publication with color drawings will be provided by the Office upon request and payment of the necessary fee.

FIG. 4: Examples of CD95L expression levels in glioblastoma tissue sections according to Example 3. Examples of high expression (CD95L positive) and low CD95L expression (CD95L negative) are given. The panel shows two examples for each expression level.

FIG. 5: Comparison of purified anti-CD95L monoclonal rabbit antibodies. A) Non reduced SDS-Page/Silver staining of purified anti-CD95L rabbit monoclonal antibodies. Lane 1 shows recombinant antibody (APG1181) purified after expression in HEK-cells. Lane 3 shows purified antibody purified form the supernatant of the rabbit hybridoma clone 24-8.

Figure 1:
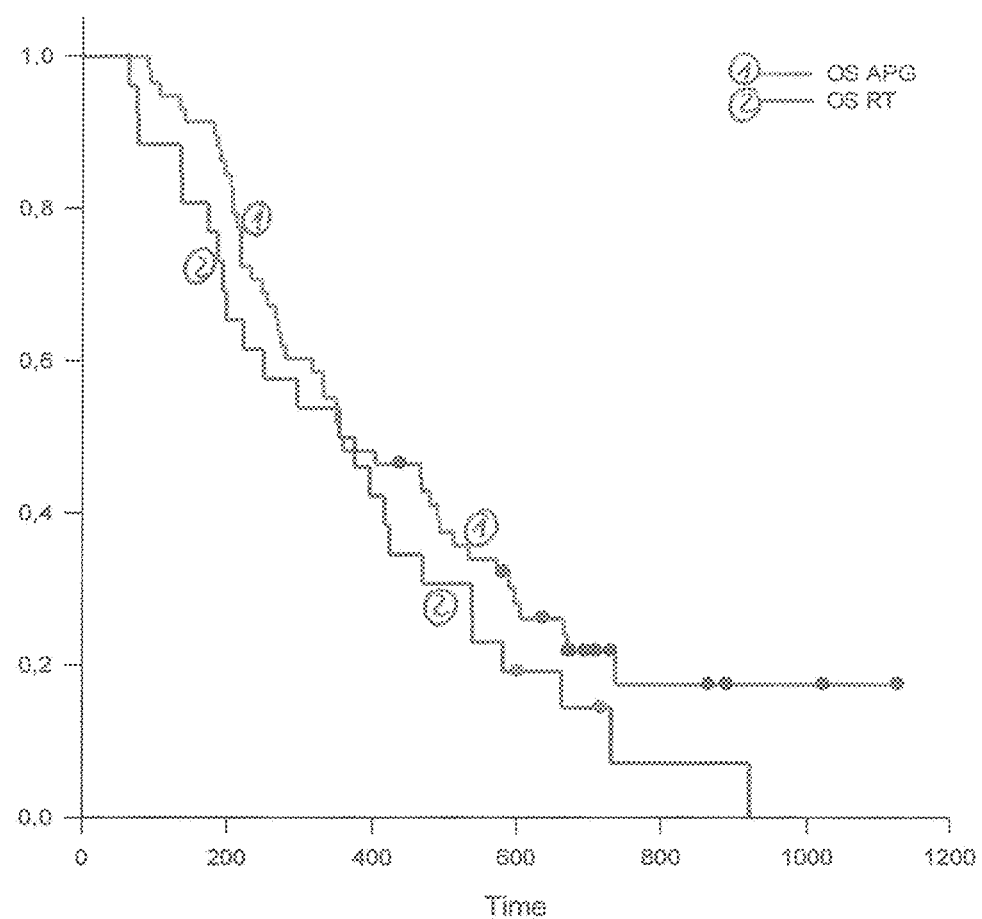
FIG. 1: Survival analysis (Kaplan-Meier plot) of GBM patients randomized to the radiation therapy (RT) only group (control group) and the radiation therapy plus APG101 group (test group). (1) Test group. (2) Control group. Abscissa: survival time (days). Ordinate: survival rate. A survival rate of 1.0 indicates 100% survival.

B) ELISA analysis of purified antibodies: APG1181 and antibody from clone 24-8 were analysed for their specificity to recognise the immobilized CD95L-peptide (CD95L-NT_1-21) used for immunization of the rabbits. Both antibodies specifically bind to the immobilized peptide. The specific recognition for both antibodies was confirmed by competition by the addition of the epitope specific peptide (+specific peptide). However, an unspecific peptide has no significant competing effect for both antibodies.

No difference in specificity or sensitivity could be seen between APG1181 and clone 24-8

FIG. 6: Specificity of anti-CD95L rabbit monoclonal antibody in IHC-based analysis. Human tonsil sections, known to express CD95L in a subset of plasma cells were analyzed with the purified antibody from clone 24-8 in the absence or presence of the specific peptide (CD95L-NT_1-21) as indicated. The specific signal seen in the absence (clone 24-8) of the peptide is entirely missing in the presence of the competing peptide confirming the specificity of the antibody.

FIG. 7: Comparison of purified antibodies anti-CD95L monoclonal rabbit antibodies. Purified antibodies APG1181 and antibody from clone 24-8 were analysed for their specificity to recognise CD95L in IHC-analysis on glioblastoma sections. For the analysis two glioblastoma sections were chosen that were previously analysed as CD95L-negative or CD95L-positive, respectively, using a commercial polyclonal anti-CD95L antibody. As seen in the figure no difference in specificity or sensitivity could be seen between APG1181 and clone 24-8 in IHC-based analysis of glioblastoma tissue.

FIG. 8: Peptides used for epitope mapping of the CD95L-antibody.

The peptides shown were used for the identification of the epitope of the anti-CD95L rabbit monoclonal antibody. The peptides encode an N-terminal part of the human CD95L. The first peptide (CD95L-NT_1-21, SEQ ID NO: 15) was used for the immunization of rabbits for the generation of rabbit monoclonal antibodies. The shorter, truncated versions (peptides 2-7, SEQ ID NOs: 16-21) and the respective permutated peptides (8-11, SEQ ID NOs: 22-25) were used for fine mapping of the epitope of individual antibodies.

FIG. 9: Epitope mapping of anti-CD95L rabbit monoclonal antibody (APG1181).

For the epitope mapping the respective peptides (see FIG. 8) were coupled to BSA, the peptide-BSA-conjugates (as indicated) were immobilized to an ELISA plate and incubated with the recombinant anti-CD95L rabbit monoclonal antibody (APG1181) followed by a specific peroxidase-conjugated anti-rabbit secondary antibody. As shown in the figure APG1181 specifically recognises an epitope that encodes the N-terminal aa13-19 of human CD95L.

FIG. 10: Fine mapping of the epitope for anti-CD95L rabbit monoclonal antibody (APG1181).

Peptide-BSA-conjugates (as indicated) were immobilized to an ELISA plate and incubated with the recombinant anti-CD95L rabbit monoclonal antibody (APG1181) followed by a specific peroxidase-conjugated anti-rabbit secondary antibody.

(A) As shown APG1181 specifically recognizes an epitope that encodes the N-terminal aa13-19 of human CD95L. Using permutated peptides (8-11 FIG. 8) for fine mapping of the epitope reveals the Y(tyrosine) in position 13 is absolutely required for defining the specificity of the respective antibody APG1181/24-8. The W(tryptophan) in position 14 and the A (alanin) in position 19, respectively, do only have a marginal influence on the binding specificity (epitope) of the antibody.

(B) A different antibody (clone 39-9) that recognizes a similar epitope but does not have the absolute requirement for the "Y" in position 13, does surprisingly show no specific reactivity towards CD95L in IHC-based analysis.

FIG. 11: Comparison of the specificity of anti-CD95L rabbit monoclonal antibodies in IHC-based analysis.

Purified antibodies from clone 24-8 and clone 39-9 were analyzed for their ability to detect CD95L in a subset of plasma cells on human tosil sections. Although both antibodies share a similar epitope, clone 39-9 does surprisingly show no reactivity towards CD95L in IHC-based analysis. Based on this result it can be concluded that the "Y" in position 13 is a prerequisite for IHC reactivity of clone 24-8.

EXAMPLE 1

APG101 (CD95 Ligand Inhibitor) for Treatment of Cancer: A Phase II Study

The phase II study was a randomised, open-label, multicentre study of weekly APG101 plus re-irradiation (APG101+RT group, test group) versus re-irradiation alone (RT group, control group) in the treatment of patients with first or second relapse or progression of glioblastoma. In total, 91 patients were included in the study. The ITT population consisted of 84 patients, 58 in the APG101+RT group and 26 in the RT group. Male and female patients with glioblastoma at first or second relapse either not being eligible for tumor resection or having macroscopic residual tumor after resection were candidates for this study. Eligible patients must have failed standard treatment that must have included radiotherapy (60Gy) and temozolomide and had to be a candidate for re-irradiation. Patients included in the study received either re-irradiation alone or re-irradiation plus 400 mg APG101 administered as a 30 min i.v. infusion once every week until progression.

Archived tumor tissue for histological analyses was available from 81 patients (of the ITT population) to confirm glioblastoma diagnosis. For the central histology review, biopsy or surgery material embedded in paraffin must have been available for central review in order to confirm the primary diagnosis of glioblastoma. All samples that were obtained were archived samples originating from the initial surgery and disease diagnosis or pre-study surgical resections. Following registration of the patient, a paraffin embedded tumor sample was collected by the study centre. Tissue sections were prepared from these tumor samples to assess various "markers" including CD95L using immunohistochemical staining (IHC).

The glioblastoma multiforme (GBM) patients participating in this clinical study were randomized into the control group and a test group.

Results

FIG. 1 describes the survival rate of the patients of the control group and the test group (overall survival rate, OS). The figure indicates that the patients of the test group receiving APG101 and radiation therapy have an improved survival rate compared with the control group receiving radiation therapy only (see Table 1).

TABLE 1

| | overall survival in all patients | |
|---|---|---|
| | RT only (OS rates) | APG + RT (OS rates) |
| 6 m | 77% | 90% |
| 12 m | 50% | 50% |
| 18 m | 23% | 34% |
| 24 m | 7.3% | 22% |

Sections of GBM tumor samples of the control group patients and the test group patients were analysed for the presence of CD95 ligand (CD95L) by immunohistolochemical staining (see Example 2).

It was surprisingly found that the level and distribution of CD95L expression strongly differed among the patients. About one third of patients exhibited a strong positive CD95L expression in the tumor tissue. Yet another third of patients exhibited a CD95L negative phenotype. The remaining patients showed a slight expression of CD95L. This phenotype could be termed "low positive" phenotype.

In the test group patients receiving APG101 on top of radiation therapy (N=58), 18 patients exhibited the strong positive CD95L expression phenotype in the tumor tissue. 18 patients exhibited the CD95L negative phenotype. In the control group (N=26), 10 patients showed the strong positive CD95L phenotype, and 9 patients showed the CD95L negative phenotype (Table 2).

TABLE 2

Overall survival times of the test group (APG101 on top of radiation therapy, "APG + RT") and in the control group (radiation therapy only, "RT only").

| | CD95Lpos. | | | CD95L neg. | | |
|---|---|---|---|---|---|---|
| | N | 95% (−/+) | median | N | 95% (−/+) | median |
| APG + RT | 18 | 200/500 | 350 | 18* | 140/670 | 410 |
| RT only | 10 | 59/440 | 250 | 9 | 190/740 | 460 |

* 3 patients censored in the APG group (still alive)
N: number of patients. The median is given in days. "95% (−/+)" indicates the 95% confidence interval.

Surprisingly, the overall survival time of the control group GBM patients was negatively correlated with the level of CD95L expression. The patients showing the strong CD95L positive phenotype of GBM had a worse prognosis than patients with CD95L negative GBM. CD95L positive patients survived 250 days, wherein CD95L negative patients survived 460 days (see Table 2).

In the test group, the patients showing the strong CD95L positive phenotype of GBM benefited from the treatment. CD95L positive patients survived 350 days.

Figure 2:
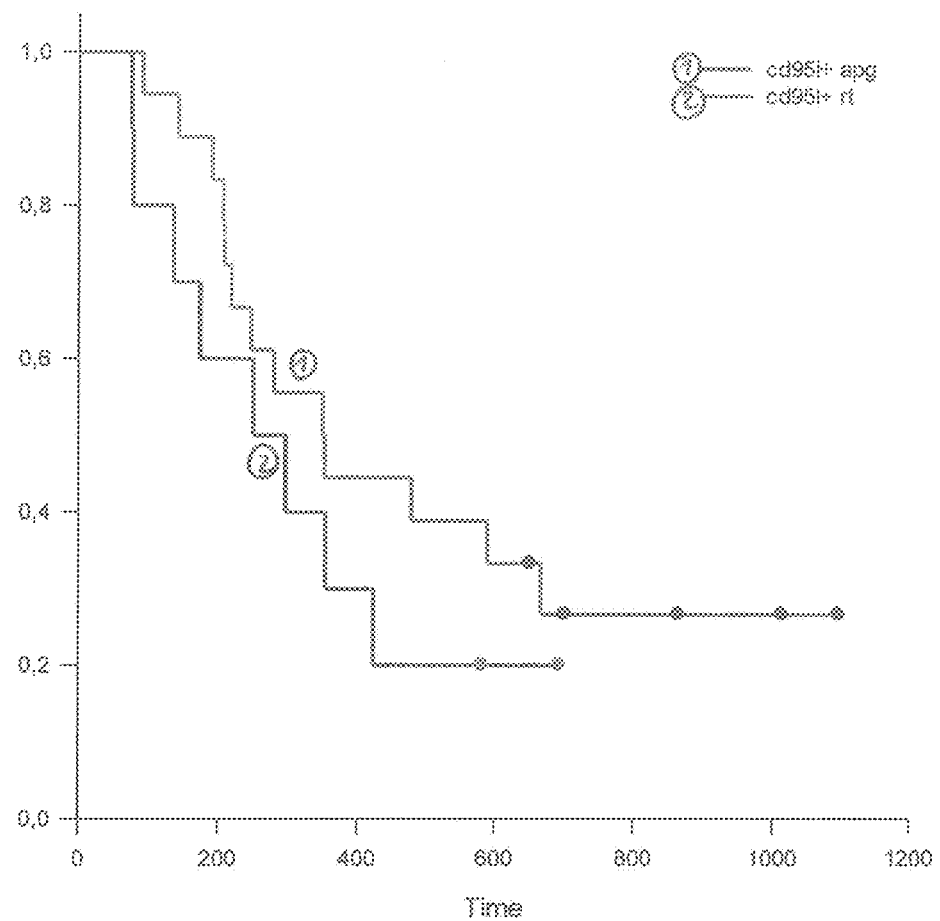
FIG. 2: Comparison of the survival data of the subgroup of CD95L positive patients taken from the patients described in FIG. 1 (Kaplan-Meier plot). (1) Test group, radiation therapy plus APG101. (2) Control group, radiation therapy only. Abscissa: survival time (days). Ordinate: survival rate. A survival rate of 1.0 indicates 100% survival.

The Kaplan-Meyer plot of FIG. 2 compares the survival data obtained in CD95L positive patients in the control group and the test group. Upon treatment with APG101, the curve is shifted to larger survival times. This means that patients showing the CD95L positive phenotype of GBM benefited from the administration of APG101. The median overall survival time increased from 250 days (control group) to 350 days.

Figure 3:
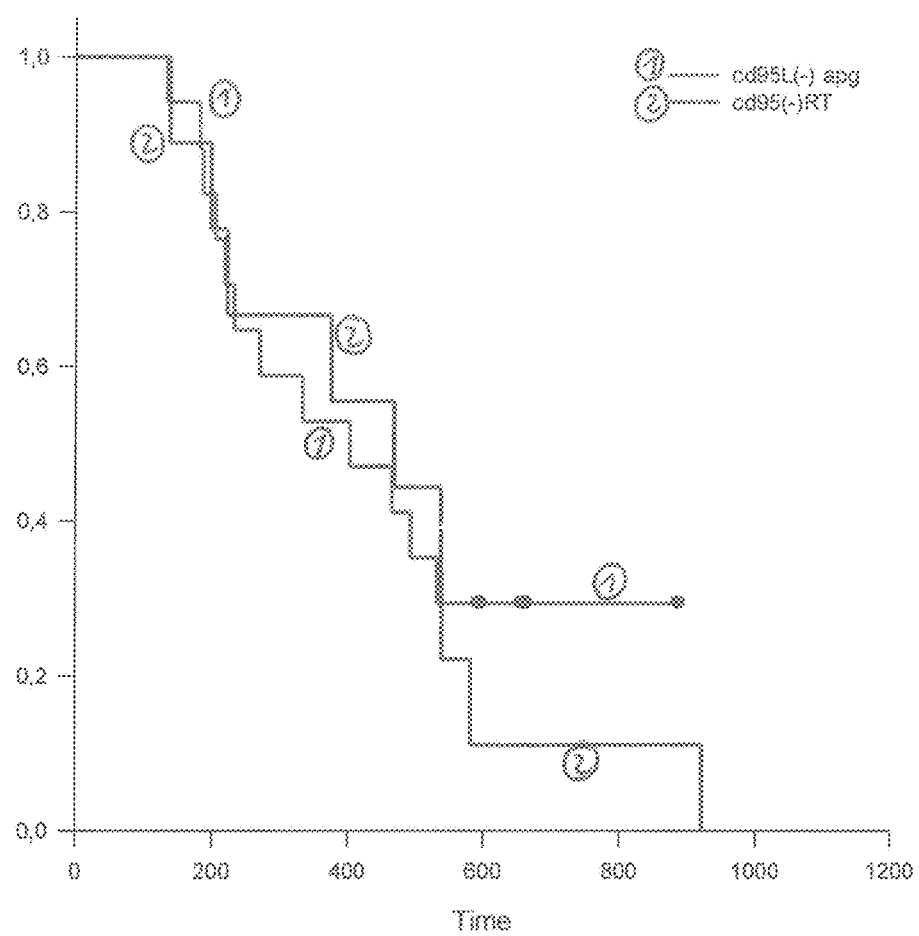
FIG. 3: Comparison of the survival data of the subgroup of CD95L negative patients taken from the patients described in FIG. 1 (Kaplan-Meier plot). (1) Test group, radiation therapy plus APG101. (2) Control group, radiation therapy only. Abscissa: survival time (days). Ordinate: survival rate. A survival rate of 1.0 indicates 100% survival.

In the test group, median overall survival in CD95 negative patients was 410 days. In comparison to the control group patients showing the negative CD95L phenotype, the median overall survival decreased from 460 to 410 days upon treatment with APG101. The data are described in the Kaplan-Meyer plot of FIG. 3. This figure indicates that the curves of the test group and the control group are largely overlapping and not statistically significant.

Summary

This example demonstrates that the expression of CD95L in cancer is associated with a reduced survival of the patients. This means that CD95L is suitable as a prognostic factors in cancer. This is important in particular in those cancer types which express CD95L to a variable extent, for example glioblastoma. Therefore, the present invention enables a diagnostic differentiation of cancer by expression of CD95L. This leads to a new diagnostic differentiation of cancer, for example glioblastoma, in CD95L positive cancer and CD95L negative cancer.

Furthermore, this example surprisingly demonstrates that a CD95L inhibitor, for example APG101, can improve the survival of cancer in patients suffering from a cancer expressing CD95L. In contrast, patients suffering from a cancer which does not express CD95L, do not benefit from the treatment with a CD95L inhibitor. This example enables a therapeutic strategy comprising determining the CD95L expression in a cancer sample, and treating the patient if CD95L is expressed. This strategy is advantageous, because the CD95L inhibitor can be administered to those patients in which a therapeutic success can be expected. This is not a disadvantage for patients suffering from a cancer not expressing CD95L, because these patients probably do not benefit from a treatment with a CD95L inhibitor.

EXAMPLE 2

Immunohistochemical Determination of CD95L

CD95L can be determined in a tissue section (for example a tumor tissue section) by performing the following procedure:

Tissue samples were fixed in 4% buffered formaldehyde and embedded in paraffin.
3 μm thick sections were dewaxed:
1. Xylol 10 min.
2. Xylol 10 min.
3. Xylol 10 min.
1. Ethanol 100% 5 min.
2. Ethanol 100% 5 min.
Ethanol 96% 5 min.
Ethanol 90% 5 min.
Ethanol 70% 5 min.
1. $H_2O$ dest. 1 min
2. $H_2O$ dest. 5 min.
High temperature antigen demasking procedures:
Citrat pH 6.0 (Target Retrieval Solution), 99° C., (DAKO, Cat. No. S1699), 25 min.
  Cooling 15 min at room temperature
  Washing 2× 5 min in PBS
  For tissue with high endogenous biotin: Biotin-Block (DAKO, Biotin Blocking System, X0590), for example for samples obtained from pancreas, liver, kidney,
    Avidin 10 min. room temperature (RT)
    Rinse in PBS 1×5 min
    Biotin 10 min. RT
    Rinse in PBS 1×5 min
  To block unspecific antibody binding, sections were incubated with blocking solution 1 (PBS, BSA 20 mg/ml; Serva, Germany, Cat. No. 11924), human IgG 1 mg/ml, (Gammunex 10%, Talecris) for 20 min.
  $1^{st}$ Antibody diluted in blocking solution 1
    Anti CD95L polyclonal rabbit (Dianova, Cat. No. DLN-14047) 1:100
    Rabbit IgG isotype control (Invitrogen (Zytomed), Cat. No. 08-6199)
  Incubation 60 minutes at room temperature.
  Washing 2× 5 min in PBS
  Blocking with blocking solution 2 for 20 minutes. Blocking with blocking solution 2=blocking with blocking solution 1+20% normal goat serum, Dianova, Cat. No. 005-000-121.
  $2^{ndary}$ antibody diluted in blocking solution 2, for example
    Goat $F(ab')_2$ Anti_Rabbit IgG (H+L chain) biotinylated, (SouthernBiotech, Cat. No. 4052-08) 1:100, Incubation 30 minutes at room temperature
  Washing 2× 5 min in PBS
  Streptavidin-alkaline phosphatase (Concentrated AP label, BioGenex, Cat:No. HK321-UK), diluted in blocking solution 1, incubation 30 minutes at room temperature
  Washing 2× 5 min in PBS
  Incubation with alkaline phosphatase substrate (DAKO Liquid Permanent Red, DakoCytomation GmbH, Glostrup, Denmark, Cat. No. K0640)
  Counterstaining with hematoxylin (Merck, Mayers Hämalaunlösung Cat. No. 1.09249.0500)
  Determination of the number of stained cells with respect to the total number of cells (% CD95L positive cells), or/and the size of the stained area with respect to the total area (% CD95L positive area). If tumor tissue is examined: determination of the number of stained tumor cells with respect to the total number of tumor cells (% CD95L positive tumor cells), or/and the size of the stained area of tumor tissue with respect to the total area of tumor tissue (% CD95L positive area of tumor tissue). Non-tumor tissue is disregarded.

EXAMPLE 3

Evaluation of CD95L Immunohistochemically Stained Slides

1. General Aspects

All CD95L-stained slides (see Example 2) were evaluated by a single board-certified neuropathologist with extensive experience in the field of neuro-oncology (C.H.). The whole evaluation was performed slide-by-slide in a single session. The longest intermission in the whole evaluation process was not longer than 60 min in between. The neuropathologist was blinded for the clinical data of the patients. The same neuropathologist had generated the reference histology diagnosis based on H&E- and silver staining combined with Mib1-, GFAP- and IDH1 R132H immunohistochemistry before. However, at the time of CD95L-evaluation these diagnosis-related slides were not available. The neuropathologist only had personal notices available about the diagnosis. Furthermore, the neuropathologist had evaluated the MGMT status and results from this analysis were known when the CD95L slides were assessed.

2. Generation of Calibration Figures

The CD95L immunohistochemistry staining was established by the company Apogenix. The evaluating neuropathologist (C.H.) was not involved in the technical aspects of the stainings, he was blinded regarding the protocols that were applied. After finalization of the CD95L immunohistochemistry establishing process a small number of CD95L-stained slides were committed to the neuropathologist to check for the quality. The neuropathologist confirmed that the applied immunohistochemistry allows high quality results and agreed to define this protocol to be the standard for further CD95L stainings. Based on these slides that were generated for quality assessment calibration figures were created that allowed comparison of CD95L immunohistochemistry intensities. Pictures were taken on a Carl Zeiss AxioPlan2 microscope with an AxioCamHR digital camera using the software AxioVision 4.8. The unmodified pictures were directly incorporated in CorelDraw v14.0 and arranged. Two pictures from different samples of similar CD95L immunohistochemistry intensities were set in one line. In summary, 2 lines of pictures representing the CD95L immunohistochemistry intensities "CD95L positive (high)" or "CD95L negative (low)" were generated (see FIG. 4).

3. Overview and Tissue Selection

In a first step the slide was scanned under the microscope (Olympus BX46) with low resolution to evaluate the amount of solid tumor tissue. Areas of normal brain parenchyma and areas of tumor infiltration were excluded from further analysis. Tumor tissue was selected for further evaluation if the following criteria were fulfilled:

Tumor tissue that appeared to be vital without signs for hypoxic damage.

Tumor tissue without resection-induced fresh bleedings.

Tumor tissue without signs of cutting-induced artifacts.

4. Single Slide Evaluation—Criterion 'Intensity'

The suitable tumor tissue of each slide was evaluated regarding the CD95L positive or CD95L negative staining intensities. The CD95L calibration figure was used to standardize the evaluation. Because most tumors showed different staining intensities in separate areas the percentage of these summed areas were counted. Each tumor was assigned a specific value in percent representing the area showing CD95L positive or CD95L negative staining intensity:

| Intensity | Percentage |
| --- | --- |
| Absent (CD95L negative) | <2% |
| CD95L positive | >5% |

Finally, the results were noticed in central pathology review form.

5. Single Slide Evaluation—Criterion 'Distribution Pattern'

A glial tumor (for example a glioblastoma) is composed of tumor cells and a fibrillary matrix of tumor cell processes. Using a light microscope these processes usually cannot be assigned to a particular tumor cell. If CD95L antibody binding was predominately seen in such cellular compartment of the matrix the staining pattern was defined to be 'diffuse'. If instead clearly tumor cells were CD95L-labeled the staining pattern was defined to be 'focal'. If essentially no CD95L labeling was observed in the tumor tissue, or the CD95L positive area was below 2% of tumor tissue, the distribution pattern was not evaluated. Finally, the results were noticed in central pathology review form.

6. Reporting of CD95L Results

Results from the CD95L evaluation were noticed in the central pathology review form (see above). The form was dated and signed by the responsible neuropathologist.

7. Generation of a Specific CD95L-Antibody Suited for IHC-Based Analysis

CD95L specific rabbit monoclonal antibodies employing immunization of rabbits with a synthetic N-terminal peptide, encoding the first 21aa of human CD95L (CD95L_NT 1-21: MQQPFNYPYPQIYWVDSSASS) were developed. For the selection of an appropriate antibody suited for the detection of CD95L in an IHC-based assay, a thorough characterization of candidate anti-CD95L rabbit monoclonal antibodies including IHC-analysis was performed. The screening process identified numerous antibodies that specifically recognized the N-terminal peptide used for immunization. However, one rabbit monoclonal antibody "clone 24-8" was in particular suited for the detection of CD95L in IHC-based analysis.

To ensure constant antibody supply recombinant expression of the antibody derived from clone 24-8 was employed in HEK cells. The recombinant antibody derived from clone 24-8 is based on the sequence of the respective IgG heavy and light chain and was designated APG1181. The specificity of the recombinant antibody is identical to the antibody derived from the hybridoma clone 24-8 (see FIG. 5 and FIG. 7). The specificity of the antibody was characterized by ELISA, IHC-analysis and mapping of the specific epitope.

The invention claimed is:

1. A monoclonal anti-CD95L antibody or a functional fragment thereof, comprising: a heavy chain comprising a CDRH1 as shown in SEQ ID NO: 1, a CDRH2 as shown in SEQ ID NO: 2, and a CDRH3 as shown in SEQ ID NO: 3, and a light chain comprising a CDRL1 as shown in SEQ ID NO: 4, a CDRL2 as shown in SEQ ID NO: 5, and a CDRL3 as shown in SEQ ID NO: 6.

2. The monoclonal anti-CD95L antibody or a functional fragment thereof according to claim 1, comprising:
a heavy chain variable region comprising the amino acid sequence as shown in SEQ ID NO: 7, or an amino acid sequence having a sequence identity of at least 95% thereof, and/or a light chain variable region comprising the amino acid sequence as shown in SEQ ID NO: 8, or an amino acid sequence having a sequence identity of 95% thereof.

3. The monoclonal anti-CD95L antibody or a functional fragment thereof according to claim 1, comprising a heavy chain comprising the amino acid sequence as shown in SEQ ID NO: 9, or an amino acid sequence having a sequence identity of at least 95% thereof, and/or a light chain comprising the amino acid sequence as shown in SEQ ID NO: 10, or an amino acid sequence having a sequence identity of at least 95% thereof.

4. The monoclonal antibody according to claim 1, wherein a label group is covalently attached to the antibody.

5. A pharmaceutical composition comprising the antibody according to claim 1, optionally together with a pharmaceutically acceptable carrier.

6. The monoclonal antibody according to claim 1, which is a full-length immunoglobulin or a functional immunoglobulin fragment selected from the group consisting of Fab, Fab', F(ab')2, Fv, and single chain antibodies (scFv).

7. The monoclonal antibody according to claim 2, which is a full-length immunoglobulin or a functional immunoglobulin fragment selected from the group consisting of Fab, Fab', F(ab')2, Fv, and single chain antibodies (scFv).

8. The monoclonal antibody according to claim 5, which is a full-length immunoglobulin or a functional immunoglobulin fragment selected from the group consisting of Fab, Fab', F(ab')2, Fv, and single chain antibodies (scFv).

9. The monoclonal antibody according to claim 2, wherein a label group is covalently attached to the antibody.

10. The monoclonal antibody according to claim 5, wherein a label group is covalently attached to the antibody.

11. The monoclonal antibody according to claim 2, comprising a heavy chain variable region comprising the amino acid sequence having a sequence identity of at least 98% to the amino acid sequence of SEQ ID NO: 7, and/or a light chain variable region comprising the amino acid sequence having a sequence identity of at least 98% to the amino acid sequence of SEQ ID NO: 8.

12. The monoclonal antibody according to claim 5, comprising a heavy chain variable region comprising the amino acid sequence having a sequence identity of at least 98% to the amino acid sequence of SEQ ID NO: 9, and/or a light chain variable region comprising the amino acid sequence having a sequence identity of at least 98% to the amino acid sequence of SEQ ID NO: 10.

* * * * *